(12) United States Patent
Adato et al.

(10) Patent No.: US 9,897,542 B2
(45) Date of Patent: Feb. 20, 2018

(54) INFRARED ABSORPTION SPECTROSCOPY

(71) Applicant: ECOLE POLYTECHNIQUE FEDERALE DE LAUSANNE (EPFL), Lausanne (CH)

(72) Inventors: Ronen Adato, Boston, MA (US); Hatice Altug, Lausanne (CH)

(73) Assignee: ECOLE POLYTECHNIQUE DEDERALE DE LAUSANNE (EPFL), Lausanne (CH)

( * ) Notice: Subject to any disclaimer, the term of this patent is extended or adjusted under 35 U.S.C. 154(b) by 451 days.

(21) Appl. No.: 14/336,537

(22) Filed: Jul. 21, 2014

(65) Prior Publication Data

US 2016/0018263 A1 Jan. 21, 2016

(51) Int. Cl.
*G01J 5/02* (2006.01)
*G01N 21/552* (2014.01)
*G01N 21/65* (2006.01)
*G01N 21/05* (2006.01)
*G01N 21/3577* (2014.01)

(52) U.S. Cl.
CPC ......... *G01N 21/554* (2013.01); *G01N 21/658* (2013.01); *G01N 21/05* (2013.01); *G01N 21/3577* (2013.01)

(58) Field of Classification Search
CPC .................. G01N 21/658; G01N 21/554
See application file for complete search history.

(56) References Cited

U.S. PATENT DOCUMENTS

| | | | | |
|---|---|---|---|---|
| 2008/0218761 A1* | 9/2008 | Nishikawa | ............. | G01N 21/05 356/445 |
| 2012/0281212 A1* | 11/2012 | Fattal | ................... | G01N 21/658 356/301 |
| 2013/0148194 A1* | 6/2013 | Altug | ................... | G01N 21/658 359/350 |
| 2014/0204373 A1* | 7/2014 | Mazzio | ................. | G01J 3/0291 356/301 |

OTHER PUBLICATIONS

Adato et al., "In-situ ultra-sensitive infrared absorption spectroscopy of biomolecule interactions in real time with plasmonic nanoantennas," Nature Communications, Jul. 23, 2013, DOI:10/1038/ncomms3154, 10 pages.
Adato et al., "Ultra-sensitive time-resolved infrared spectroscopy of biomolecule interactions with plasmonic nanoantennas," Optical Society of America, 2014, 2 pages.

* cited by examiner

*Primary Examiner* — Kenneth J Malkowski
(74) *Attorney, Agent, or Firm* — Andre Roland S.A.; Nikolaus Schibli

(57) ABSTRACT

The present invention relates to an infrared absorption spectroscopy apparatus including an infrared transparent substrate comprising a first and second surface, an array of plasmonic nano-antennas arranged on the first surface of the infrared transparent substrate, a flow cell for holding a liquid to allow spectroscopy measurements in a liquid environment, the array of plasmonic nano-antennas being located inside the flow cell, an optical source providing an incident light probe signal incident on at least a part of the array of plasmonic nano-antennas via the second surface of the infrared transparent substrate, and an optical element to collect reflected light signal reflected by said part of the array of plasmonic nano-antennas.

26 Claims, 10 Drawing Sheets

INFRARED ABSORPTION SPECTROSCOPY

BACKGROUND OF THE INVENTION

The present invention relates to infrared absorption spectroscopy of molecules and, in particular, to In-Situ Ultra-Sensitive infrared absorption spectroscopy of biomolecules and biomolecule interactions in real-time with Plasmonic Nanoantennas.

Infrared absorption spectroscopy is a powerful biochemical analysis tool as it extracts detailed molecular structural information in a label-free fashion. Its molecular specificity renders the technique sensitive to the subtle conformational changes exhibited, for example, by proteins in response to a variety of stimuli. Yet, sensitivity limitations and the extremely strong absorption bands of liquid water severely limit infrared spectroscopy in performing kinetic measurements in biomolecules' native, aqueous environments.

Infrared (IR) absorption spectroscopy directly probes the vibrational modes associated with the various molecular bonds in a sample by measuring absorption in the mid-IR spectral region, ~3-20 μm (3000-600 $cm^{-1}$. As such, IR spectroscopy measurements are intrinsically endowed with a level of chemical specificity and information content far exceeding most other optical measurement techniques. Fluorescence based measurements rely on an exogenous label for their signal, while refractive index (RI) sensors essentially monitor a non-specific bulk property, mass accumulation. In contrast, signal in IR spectroscopy originates with the most intrinsic part of a sample—its molecular structure. IR measurements can thus be leveraged for automated tissue classification and cancer identification. Most significant is their ability to record the conformational changes of proteins that elucidate the molecular mechanisms of their function. Critically, such measurements do not involve any transfer of mass and are therefore largely inaccessible to other methods.

Despite such advantages, several shortcomings severely limit the application of IR absorption spectroscopy in the measurement of biological samples and their dynamic behavior in real-time. These are concerned with sensitivity and difficulties in sampling in aqueous solutions. Sensitivity is limited as a result of Beer's law, which implies that for the small IR absorption cross sections, in thin samples such as monolayers, absorption signals become prohibitively weak. For measurement in solution, water, though an essential component of most biological processes, presents the major obstacle. Specifically, its OH bending absorption can overwhelm any signal from protein samples. Therefore, special care to limit path lengths to less than 10 μm and protein concentrations of several tens of mg/mL are needed to obtain the high signal-to-noise (SNR) level data required for functional studies when measurements are performed in solution.

This second issue is addressed in part by attenuated total internal reflection (ATR) sampling, which achieves a fixed path length via the evanescent field used to probe the sample. Yet, without any signal amplification it cannot achieve adequate sensitivity. This fundamental limitation can be overcome by leveraging the strong light-matter interaction and sub-wavelength localization enabled by the plasmonic resonances of nano-scale metallic particles, resulting in the phenomena of surface enhanced infrared absorption (SEIRA), in analogy with surface enhanced Raman scattering (SERS). While early SEIRA studies utilized metal island films, prepared by e.g. chemical means or physical vapor deposition, these are stochastic in nature, provided limited enhancement and suffered from significant repeatability issues. In contrast, recent work has shown that explicitly engineered plasmonic nanoantennas with mid-IR resonance offer reliable, $10^4$-$10^5$ fold enhancement, occurring at well-defined deterministic locations. To date, however, all such resonant SEIRA measurements have been performed on dry samples, strongly limiting the use of powerful infrared spectroscopy for in-situ studies with live cells, tissues etc. and performing real-time measurements, i.e. biomolecular kinetic interactions important for biology, biochemistry, pharmacology.

BRIEF SUMMARY OF THE INVENTION

The present invention relates to an infrared absorption spectroscopy apparatus and an infrared absorption spectroscopy method permitting to overcome the above mentioned inconveniences. The Infrared absorption spectroscopy method includes providing an infrared transparent substrate comprising a first and second surface, an array of plasmonic nano-antennas being arranged on the first surface of the infrared transparent substrate, where the array of plasmonic nano-antennas includes a plurality of molecules; providing a flow cell holding a liquid to allow spectroscopy measurements in a liquid environment, the array of plasmonic nano-antennas being located inside the flow cell and in the liquid; providing an optical source emitting an incident light signal incident on at least a part of the array of plasmonic nano-antennas through the second surface of the infrared transparent substrate, and providing an optical element to collect reflected light reflected by said part of the array of plasmonic nano-antennas.

A plasmonic chip-based technology can be used to overcome the above mentioned challenges, enabling the in-situ monitoring of protein and nano-particle interactions at high sensitivity in real-time from very small amounts of analyte samples. The present invention leverages the plasmonic enhancement of absorption bands in conjunction with a non-classical form of internal reflection. These features not only expand the reach of infrared spectroscopy to a new class of biological interactions, but additionally enable a unique chip-based technology.

The present invention advantageously allows for the first time, the above mentioned dramatic enhancement to be applied to monitor biological samples in their native aqueous environment. Protein binding interactions can, for example, be monitored via their specific amide band absorption. Signal levels measured on monolayers 175 ng/$cm^2$ surface concentrations correspond to a surface averaged enhancement of a full order of magnitude over ATR, enabling high SNR measurements. Highlighting the exquisite chemical sensitivity of IR spectroscopy, measurements can be performed on chemically distinct particles. It is possible to chart the movement of various molecular groups, down to the displacement of minute volumes of water. Uniquely, the plasmonic system according to the present invention is also a chip-based technology that far exceeds ATR in terms of its compact nature and versatility. This is achieved by exploiting nanoantennas not only to provide the aforementioned absorption enhancement, but also to efficiently re-direct far-field radiation. Internal reflectance is thus provided here not by classical total internal reflection, but by an infinitesimally thin patterned plasmonic surface. This represents a dramatic and transformative advancement in the compatibility of IR absorption spectroscopy with modern sample preparation and handling technologies (such as microfluidics, optical trapping, high throughput scanning) as well as complementary imaging or other optical measurement techniques.

BRIEF DESCRIPTION OF THE DRAWINGS

Figure 1:
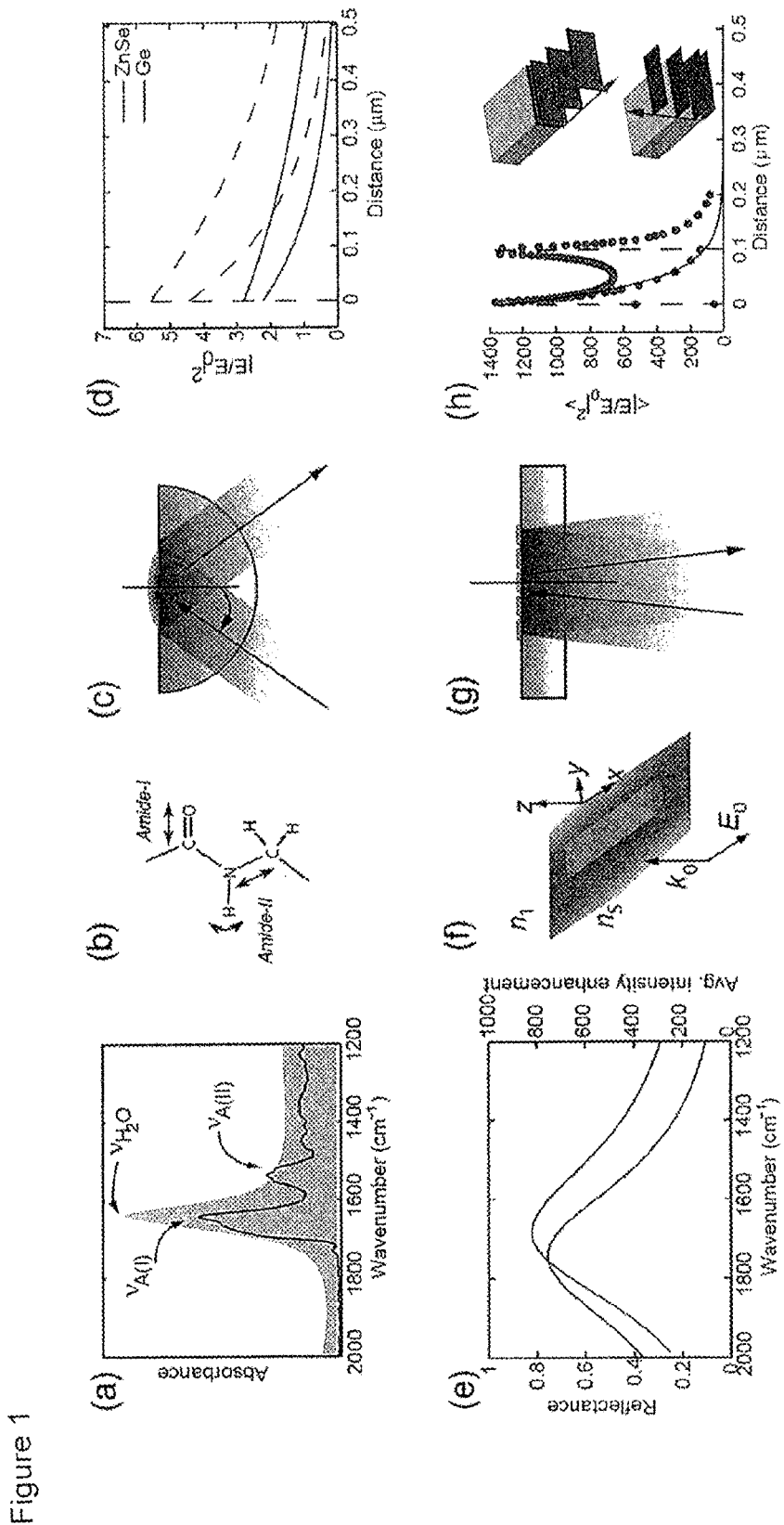
Figure 11:
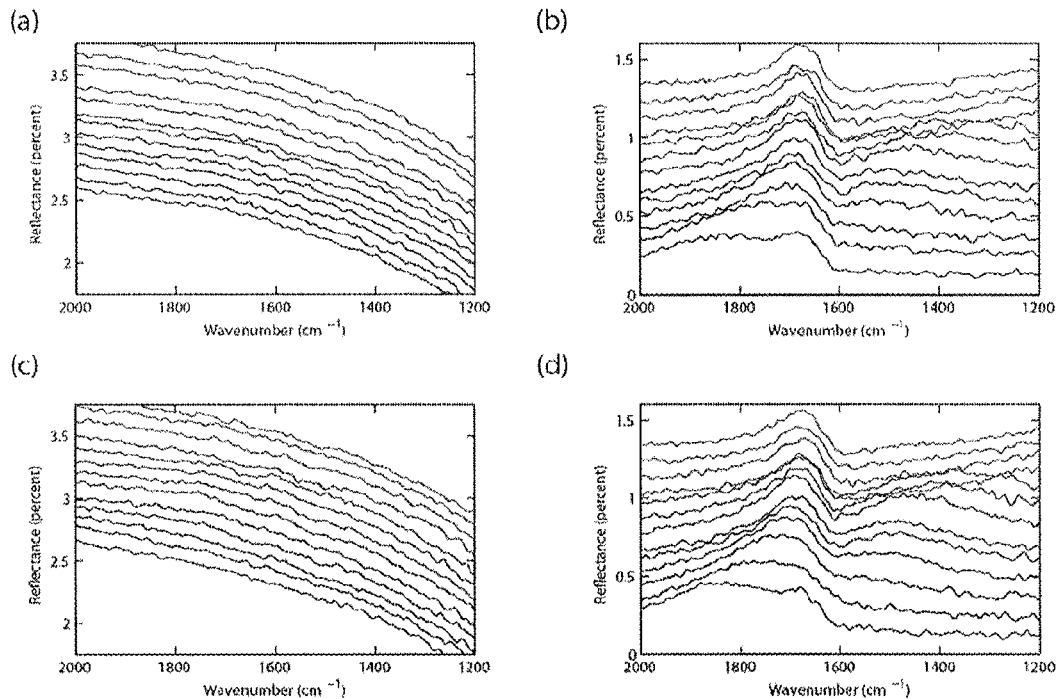
Figure 12:
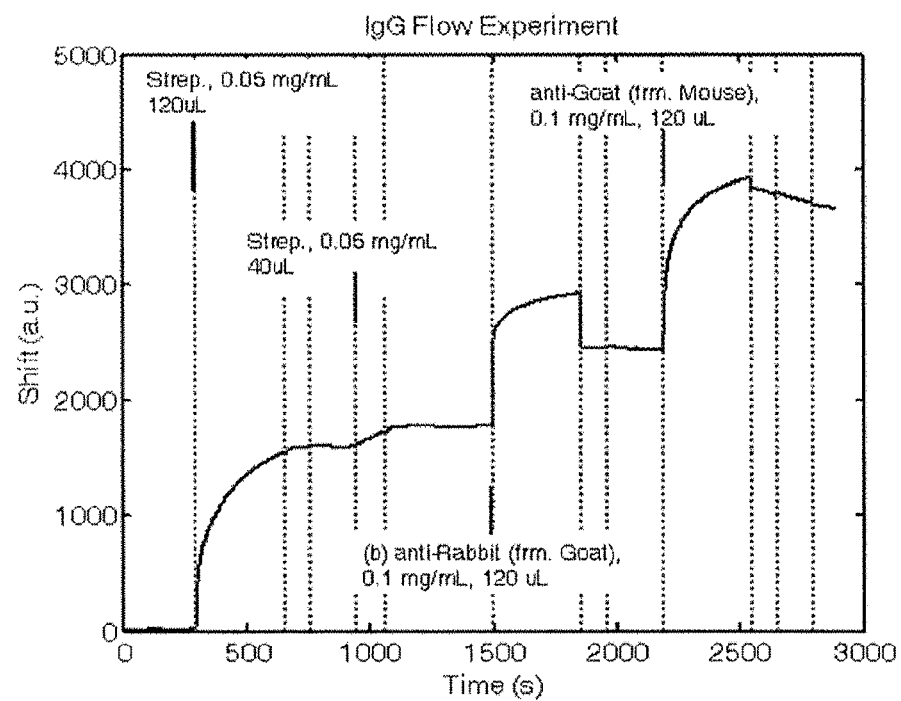

Having thus described the invention in general terms, reference will now be made to the accompanying drawings, which are not necessarily drawn to scale, and wherein:

FIG. 1a illustrates molecular bond-specific infrared absorption spectra of a protein (solid line) and liquid water (grey region);

FIG. 1b illustrates the molecular structure of the amide bond and associated vibrational modes (arrows);

FIG. 1c illustrates the geometry of a typical single-pass ATR sampling technique;

FIG. 1d illustrates the E-field intensity in the sampling region with Refractive index n=1.3;

FIG. 1e illustrates the FDTD-simulated infrared spectra of a resonant plasmonic antenna on $CaF_2$, and FIG. 1f shows the corresponding simulation geometry;

FIG. 1g illustrates a geometry for PIR sampling;

FIG. 1h illustrates a spatial profile of the enhancement in the sampling volume;

FIG. 2a illustrates the physical origin of resonances in a linear mid-infrared nanoantennas;

FIGS. 2b and 2c illustrates a generalized resonator model for particle resonance;

FIG. 2d illustrates an extension of the generalized resonator model to include the water OH-bend mode;

FIGS. 2e to 2g show a simulated antenna response and extracted characteristics;

FIGS. 2h to 2j show simulated reflectance spectra, TCMT fit, extracted resonance frequencies and damping rates for nanoantennas in an aqueous environment (full complex RI of water used);

FIG. 3a illustrates an apparatus for PIR measurements according to the present invention (flow cell and PIR chip not to scale);

FIG. 3b shows a representative scanning electron microscope image of the nanoantennas on the PIR chip (scale bar=1 µm);

FIG. 4a presents reflectance spectra measured for a set of nanoantenna arrays with different lengths as indicated in the legend of this Figure;

FIG. 4b presents reflectance spectra before (dashed) and after (solid) SA protein binding for the L=2.2 µm antenna array;

FIG. 4c presents the absorbance peak integral as a function of the nanoantenna resonance frequency (closed markers and solid lines; left y axis);

FIGS. 4d to 4f presents data analogous to that of FIGS. 4a to 4c, but for sampling in an aqueous media;

FIG. 5a is a schematic of protein-binding interactions measured in-situ with PIR-SEIRA;

FIGS. 5b to 5d presents a time series of spectra taken during SA binding (FIG. 5b), aR(G) binding (FIG. 5c) and three target IgG-binding (FIG. 5d);

FIG. 5e shows the amide band peak integral used to assess protein binding;

FIG. 5f presents the peak integral (integrated absorbance) evolution over time during the protein-binding measurements for the three samples;

FIG. 5g presents the expansion of the incremental change during the three different target IgG-binding steps;

FIG. 6a is a schematic of latex bead-SA binding;

FIG. 6b and FIG. 6c presents time-series absorbance spectra during the SA (FIG. 6b) and LB-binding steps (FIG. 6c);

FIG. 6d illustrates specific chemical structures and their corresponding infrared fingerprints (peak integrals) used to monitor their presence during flow experiments;

FIGS. 6e and 6f present the evolution of the peak integrals (integrated absorbance, units of mOD cm$^{-1}$) over time during SA- and LB-binding steps, respectively;

FIGS. 7a to 7f show experimental characterization of linear mid-IR nano-antennas for PIR spectroscopy;

FIGS. 8a to 8d show constrained base-line correction based on a peak shift;

FIGS. 9a to 9d show calculated quantities of interest for comparison with ATR sampling;

FIGS. 10a to 10b show an expanded set of measurements scanning the plasmonic resonance wavelength through the protein amide-I and II absorption bands' frequencies;

FIGS. 11a to 11d show measurements taken with 's-polarization' perpendicular to a nano-rod long axis; and FIG. 12 shows surface plasmon resonance spectroscopy on a SA monolayer and IgG binding assay.

DETAILED DESCRIPTION OF THE INVENTION

FIG. 1 illustrates the concept of PIR-SEIRA (plasmonic internal reflection (PIR) surface enhanced infrared absorption (SEIRA)) spectroscopy. FIG. 1(a) illustrates molecular bond-specific infrared absorption spectra of protein (solid line) and liquid water (grey region). The protein backbone vibrations, amide-I and II are indicated ($v_{A(I)}$ and $v_{A(II)}$) along with the H2O-bending mode ($v_{H2O}$). FIG. 1(b) shows the molecular structure of the amide bond and associated vibrational modes (arrows). FIG. 1(c) illustrates the geometry of a typical single-pass ATR sampling technique. FIG. 1(d) presents the E-field intensity in the sampling region with refractive index RI n=1.3. Calculations are shown for s and p polarizations (solid and dashed lines, respectively) and two different ATR crystal materials: ZnSe (n=2.4) and Ge (n=4.0). Light is incident at 45°. FIG. 1(e) presents FDTD-simulated infrared spectra of a resonant plasmonic antenna on $CaF_2$, and FIG. 1(f) shows the corresponding simulation geometry. Antennas are 1.8 µm long, 200 nm wide and 100 nm thick and are arranged in a square (P=2.5 µm period (from the center of one antenna to the next)) lattice. The substrate and ambient media RIs are $n_S$=1.4 and $n_1$=1.3, respectively. Reflectance and near-field enhancement are shown, where the latter corresponds the average E-field intensity over a volume defined by the end-face of the rod, extended out 10 nm. FIG. 1(g) shows a geometry for PIR sampling. Light may be incident normally, as in the FDTD simulations, or at a low angle (as in experiments). FIG. 1(h) shows the spatial profile of the enhancement in the sampling volume. Simulated E-field intensity enhancement extending out, perpendicular to the end-face of the rod or moving in the z-direction, through it. The region over which the latter is averaged extends out 10 nm from the end-face, as in FIG. 1e. Note the dramatic difference in the ordinate scale in comparison with FIG. 1d.

The concept of the plasmonic internal reflection (PIR) technique according to the present invention is detailed in FIG. 1. The basis for the chemical sensitivity of IR spectroscopy as well as the obstacle presented by water for measuring in solution is illustrated FIGS. 1a,b which shows the two major protein backbone bands, as well as the OH bending mode. ATR overcomes this issue by probing the sample through the evanescent field associated with the total internal reflection process (FIG. 1c,d).

The plasmonic approach according to the present invention is described in FIGS. 1e-h. The near-field enhancement, localization and strong far-field scattering provided by the resonances of engineered mid-IR nanoantennas form the core elements of the present invention. The numerical (finite-difference time-domain, FDTD) simulations in FIG. 1e demonstrate the resonances of gold (Au) rod shaped particles, on a calcium fluoride (CaF$_2$) substrate, to offer these key properties. Notably, the value of 80% reflectance on resonance corresponds to ~14 times the geometrical fraction of the unit cell's area occupied by the particles and points to the extremely efficient capture and re-direction of the incident light by the nanoantennas. This enables a unique and highly advantageous alternative to ATR, where light incident from the substrate side excites the nanoantennas and their strong backscattering enables internal reflectance as diagramed in FIG. 1g. This provides the opportunity to interrogate samples at the nanoantenna surface via SEIRA spectroscopy in solution, without concern for path-length, as in the ATR technique. Finally, FIG. 1h probes the spatial profile of the sampling region. The plasmonic nanoantennas confine the intensity at their tip-ends. Normal to the substrate variation of the field is moderate along the end-face of the rod but decays rapidly after passing the rod thickness. Parallel to the substrate, perpendicular to the rod end-face, the decay is exponential, with a characteristic penetration depth (decay length) of ~80 nm, indicating a dramatically enhanced surface selectivity.

Figure 2:
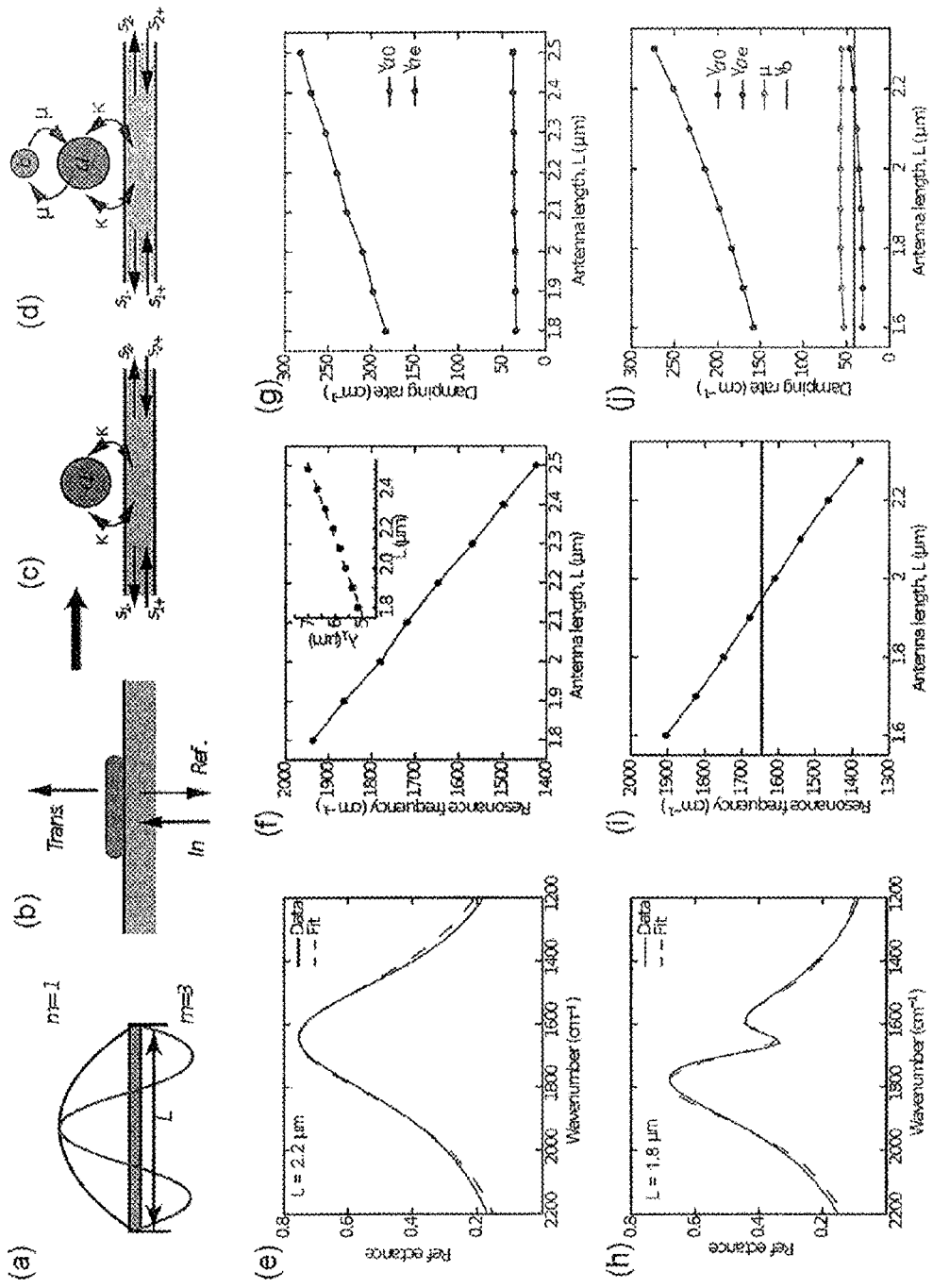

FIG. 2 illustrates linear mid-infrared nanoantennas for PIR spectroscopy. FIG. 2(a) shows the physical origin of the resonances. First- (m=1) and third- (m=3) order antenna modes associated with current oscillations in rod-shaped nano-particles are illustrated. Only odd order modes couple to normally incident far-field radiation. FIGS. 2(b,c) show a generalized resonator model for the particle resonance. The resonant mode is described with amplitude a and couples to input/output travelling waves associated with incident ($s_{1+}$), reflected ($s_{1-}$) and transmitted ($s_{2-}$) light via the coupling constant k. FIG. 1(d) shows an extension of the generalized resonator model to include the water OH-bend mode. This is accomplished by introducing a second resonant mode, with amplitude b, coupled to the plasmonic resonance via m. Three parameters: the OH-bend frequency, damping rate ($v_b$ and $\gamma_b$, respectively) and m are therefore added to the model. FIGS. 2(e-g) present the simulated antenna response and extracted characteristics. Antennas are simulated as in a dry ($n_1=1$) environment, on CaF$_2$ ($n_S=1.4$). The width and thickness are 200 and 100 nm, respectively, and P=2.75 μm. FIG. 2(e) presents reflectance for a L=2.2 μm antenna array and temporal coupled mode theory (TCMT) fit corresponding to the m=1 resonance. FIG. 2(f) presents the variation in resonance frequency with antenna length. The inset shows the linear fit to the resonant wavelength: $\lambda_1=c_1L+c_0$. The fit gives $c_1$=2.63 and $c_0$=0.37 with an $r^2$ of 0.992. FIG. 2(g) presents the radiative ($\gamma_{ae}$) and non-radiative ($\gamma_{a0}$) damping rates extracted from simulated reflectance spectra as a function of nanoantenna length. FIGS. 2(h-j) present simulated reflectance spectra, TCMT fit, extracted resonance frequencies and damping rates for nanoantennas in an aqueous environment (full complex RI of water used). The antenna cross-section is as in FIGS. 2e-g, while the periodicity is P=2.5 μm. In the fits, $v_b$ and $\gamma_b$ are fixed, whereas $v_a$, $\gamma_{ae}$, $\gamma_{a0}$ and μ are let to vary. FIG. 2(h) presents reflectance spectra and fit for a L=1.8 μm antenna array (P=2.5 μm period). FIG. 2(i) shows the extracted antenna resonance frequency. FIG. 2(j) presents the extracted antenna damping rates and the antenna OH-bend coupling parameter. The (fixed) values of $v_b$ and $\gamma_b$ are indicated by the straight lines in i and j, respectively.

Concerning plasmonic nanoantenna design, the linear rod geometry examined in FIG. 1e-h offers not only strong enhancement, but also many qualities ideal for the device concept according to the present invention.

Firstly, their resonances (FIGS. 2a,e) can readily be tuned to a vibrational mode of interest through a well characterized linear relationship between the resonance wavelength ($\lambda_m$) and the antenna length, L. Secondly, they scatter strongly on resonance leading to the high reflectance critical to the PIR system. The origin of this feature can be understood by applying the temporal coupled mode theory (TCMT) to the generalized resonator model outlined in FIGS. 2b,c. Characterizing the antenna resonance solely in terms of its center frequency ($v_a$), radiative and non-radiative damping rates ($\gamma_{a0}$ and $\gamma_{ae}$ respectively) and coupling (κ) to incoming and outgoing radiation, the reflectance can be written as, $$R(v) = \left|\frac{s_{1-}}{s_{1+}}\right|^2 = \frac{\kappa^4}{(v-v_a)^2 + (\gamma_{a0}+\gamma_{ae})^2} \quad (1)$$

where $\kappa=\sqrt{\gamma_{ae}}$ via reciprocity. Equation (1) gives a Lorentzian line-shape whose amplitude and line-width are determined by the relative contributions of the loss mechanisms. In the mid-IR, for a Drude metal such as Au, radiative damping dominates ($\gamma_{ae} \gg \gamma_{a0}$) and R(v) approaches unity.

By fitting equation (1) to numerical simulations (FIG. 2e) and extracting the resonance parameters, both the linear variation in frequency (FIG. 2f) and dominance of radiative damping (FIG. 2g) are verified. The latter is an important aspect of mid-IR plasmonics and provides the unique opportunity which PIR exploits. While these properties depend essentially on the antenna length, periodicity in nano-particle arrays can also influence properties. Here the periodicity of the array was designed such that only the zeroth order propagate and the unit cell size is commiserate with the antenna extinction cross section, which optimizes the collection efficiency and ensures equation (1) is accurate.

Equation (1) has been extended via the TCMT to include the effects of the OH bend mode. As shown schematically in FIG. 2d, this is accomplished by introducing a coupling (via μ) between the plasmonic resonance and a purely dissipative mode with center frequency and line-width ($v_b$ and $\gamma_b$ respectively) representative of the water absorption band. This is important since, while the calculations in FIG. 1 provided a general view of the concept and behavior of the our PIR platform by assuming a constant and real refractive index, water's absorption bands in the IR clearly influence the response of our nanoantennas (FIGS. 2h-j). Fitting with the analytical model therefore allows the determination of the underlying antenna parameters, important in validating and characterizing experimental data.

Figure 3:
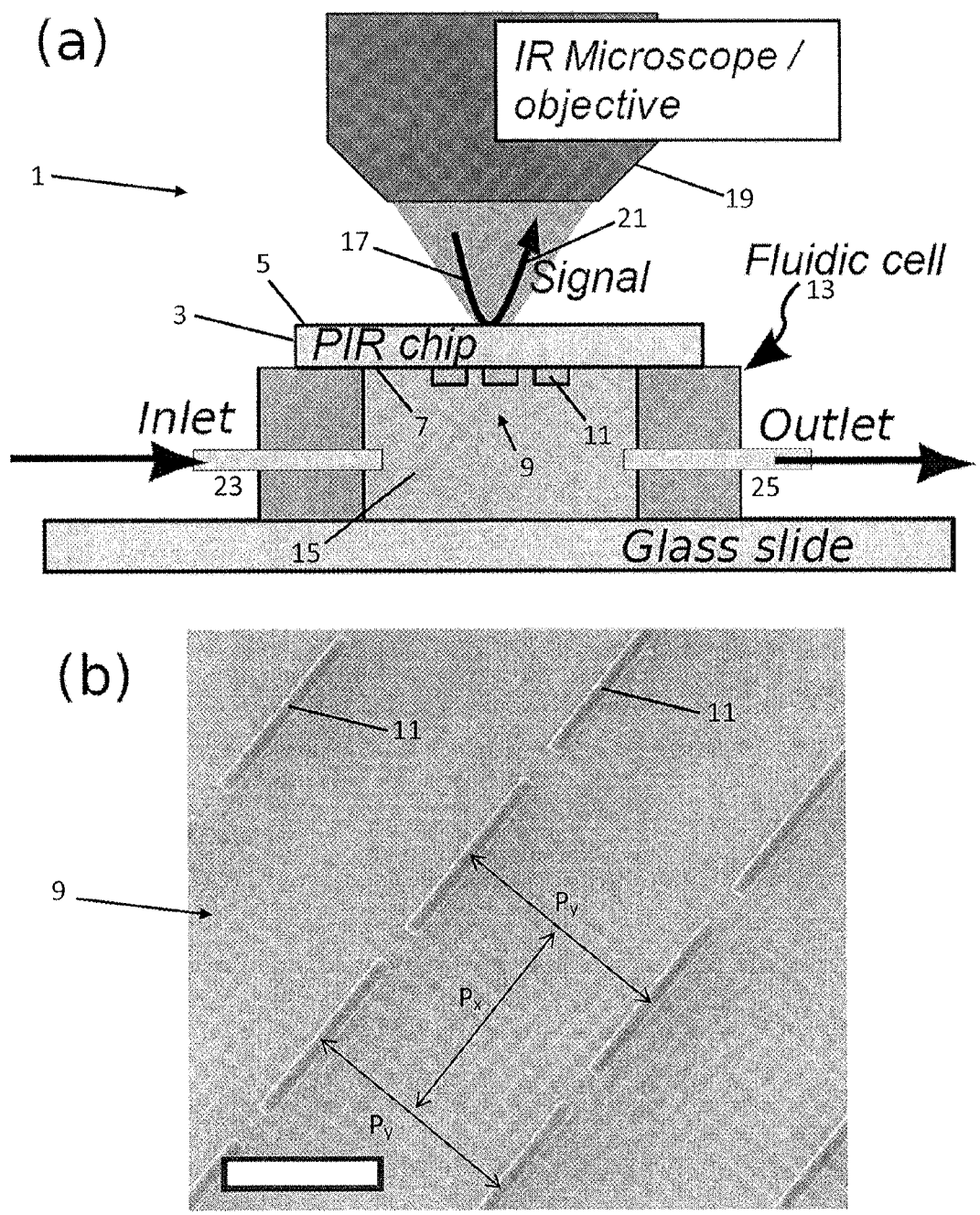

FIG. 3 illustrates an example apparatus according to the present invention and apparatus setup. The apparatus can include, for example, one or more PIR chips. FIG. 3(a) shows an example configuration for the PIR measurements (flow cell and PIR chip not to scale). FIG. 3(b) is a representative scanning electron microscope image (Scale bar, 1 μm). The illustrated exemplary antenna array parameters are all nominally consistent with those in the numerical simulations. The cross-sectional width and thickness of 200×100 nm² is maintained throughout, and the periodicities are P=2.75 and 2.5 µm for dry- and aqueous-environment measurements, respectively.

The Infrared absorption spectroscopy apparatus (or system) 1 according to the present invention includes an infrared transparent substrate 3 comprising a first 5 and second surface 7, an array 9 of plasmonic nano-antennas 11 arranged on the second surface 7 of the infrared transparent substrate 3. The first surface 5 is located opposite the second surface 7. The apparatus further includes a flow cell 13 for holding a liquid 15 to allow spectroscopy measurements in a liquid environment. The array 9 of plasmonic nano-antennas 11 being located inside the flow cell. The apparatus further includes an optical source (not-illustrated) providing an incident light probe signal 17 incident on at least a part of the array 9 of plasmonic nano-antennas 11 via the second surface 7 of the infrared transparent substrate 3. The apparatus additionally includes an optical element 19 to collect the reflected light signal 21 reflected by the above mentioned part of the array 9 of plasmonic nano-antennas 11.

Only the first surface 5 of the infrared transparent substrate 3 is in contact with the flow cell 13. The first surface 5 forms part of an inner wall of the flow cell 13. The flow cell 13 is closed on one side, for example, by a glass slide and on the other side by the infrared transparent substrate 3.

A plurality of the plasmonic nano-antennas 11 or the entire array 9 has a plurality of molecules attached thereto. A layer of molecules can be attached thereto. A monolayer or one sole layer of molecules can be attached. The molecule can, for example, be a biomolecule.

The nano-antennas 11 are not limited to the geometry, dimensions and periodicity previously mentioned. The nano-antennas 11 can have a geometry (dimensions) and array arrangement (periodicity $P_x$, $P_y$) on the infrared transparent substrate that is chosen to permit a plasmonic resonance at a frequency substantially coinciding with a frequency of the molecule on which spectroscopy measurements are being carried out, for example, a vibrational mode associated with a molecular bond of the molecules. The geometry (dimensions) and array arrangement can also be chosen to permit a plasmonic resonance at a frequency that additionally minimizes light loss due to absorption by water molecules.

The reflectance of the plasmonic nano-antennas 11 is tailored in frequency/wavelength as well as in intensity to optimize the measured signal and minimize the negative impact of the liquid (water) on the measured signal.

The nano-antennas 11 can be metallic nano-antennas or dielectric nano-antennas or formed using graphene or boron nitride.

The infrared transparent substrate can be, for example, a $CaF_2$ substrate, a diamond substrate or a sapphire substrate. It is not necessary that the substrate be fully infrared transparent. Alternatively, the substrate 3 can be a substrate that is thinned to a thickness that permits sufficient IR transmission and spectroscopy measurements to be carried out.

The flow cell 13 includes an inlet 23 and an outlet 25 for respectively introducing a liquid and/or molecules into the flow cell and removing liquid and/or molecules from the flow cell. The apparatus of FIG. 3 includes a microscope objective for focusing incident light and collecting the reflected light. However, such a microscope objective is not necessary in the excitation arm and/or the collection (detection) arm. For example, for large area applications, a microscope objective is not required to focus the incident light on the sample to be measured.

The apparatus may include, for example, a spectrometer or mid-IR detector to analyze the light signal reflected by the plasmonic nano-antennas 11.

Infrared absorption spectroscopy of the molecules is carried out using the apparatus of the present invention by directing the incident light of the optical source (for example, a broad spectral source) onto at least a part of the array 9 of plasmonic nano-antennas 11 to which the molecules have been attached. Advantageously, the light may be incident at only 0 degrees, or substantially 0 degrees (incident normally on the substrate 3).

The incident light passes through the first surface 5 of the infrared transparent substrate 3 and then the second surface 7 to arrive on the nano-antenna s 11.

The incident light strongly interacts with the attached molecules due to the plasmonic resonance of the nano-antennas 11 configured to have a resonance at a frequency or in a frequency range range that includes a frequency of the molecule on which the spectroscopy measurement is being carried out (for example, a vibrational mode associated with a molecular bond of the molecules). The light is reflected back by the nano-antennas 11 through the substrate 3 and the surface 7 and is collected, for example, by a microscope objective and directed to a spectrometer or mid-IR detector for analysis.

The use of a microscope objective is however not essential and the reflected light may be provided directly to an optical element such as a spectrometer or mid-IR detector for spectroscopic analysis.

A liquid, such as water, is provided in the flow cell and molecules can be provided via the inlet 23 for binding to the nano-antennas 11 or for binding to molecules already attached to the nano-antennas 11. This allows In-Situ Ultra-Sensitive infrared absorption spectroscopy of biomolecules and biomolecule interactions in real-time to be carried out as now detailed below. The introduced molecules flow through the flow cell via the outlet 25.

In-Situ Sampling of Protein Monolayers: the application of PIR and the sensitivity of the technique through the measurement of a protein monolayer is demonstrated in dry and aqueous environments. Comparing measurements in the two allows us to characterize for the first time the effects of the overlapping water band on the enhancement and response of the nanoantennas.

In this particular example, the PIR chips consist of nine 100×100 µm² arrays of Au nanoantennas fabricated on $CaF_2$ by electron beam lithography, the dimensions being consistent with those in the simulations (FIG. 3b). Inserting chips into a flow cell (FIG. 3a) allowed measurements in aqueous environment and, in later experiments, the introduction of analyte solutions. To probe the response to a protein monolayer, the Au antennas were functionalized with a self-assembled monolayer of a biotin labeled alkanethiol (BAT) and spotted with streptavadin (SA, 50 ug/mL). The specificity of the Au-thiol bond and high affinity of SA-biotin results in the formation of a ~5 nm thick SA monolayer over the Au surface. For reference, we prepared Au slides identically for measurement via grazing angle IRRAS. The absorbance spectra of one such sample is shown at the bottom of FIG. 4a (black curve).

The spectra of the antennas before protein binding are shown in FIGS. 4a,d in air and water respectively. Extraction of the resonance parameters as in FIG. 2 yields excellent agreement with the simulations and equation 1. Measurements performed on multiple chips show excellent repeatability (see FIG. 7). This highlights the practical importance of the controlled geometry of the nanoantennas as well as the substrate selection. The former allows highly reproducible fabrication, while $CaF_2$ is notable for its low refractive index and minimal dispersion over frequencies below 1000 cm$^{-1}$. These minimize front surface reflections that reduce throughput as well as lead to interference features. Additionally, $CaF_2$ is transparent both in the IR and visible, which enables new opportunities, not only allowing easy simultaneous visible inspection of the sampling region (which we leverage here) but also the potential for e.g. parallel fluorescence detection or integration with optical trapping.

Figure 4:
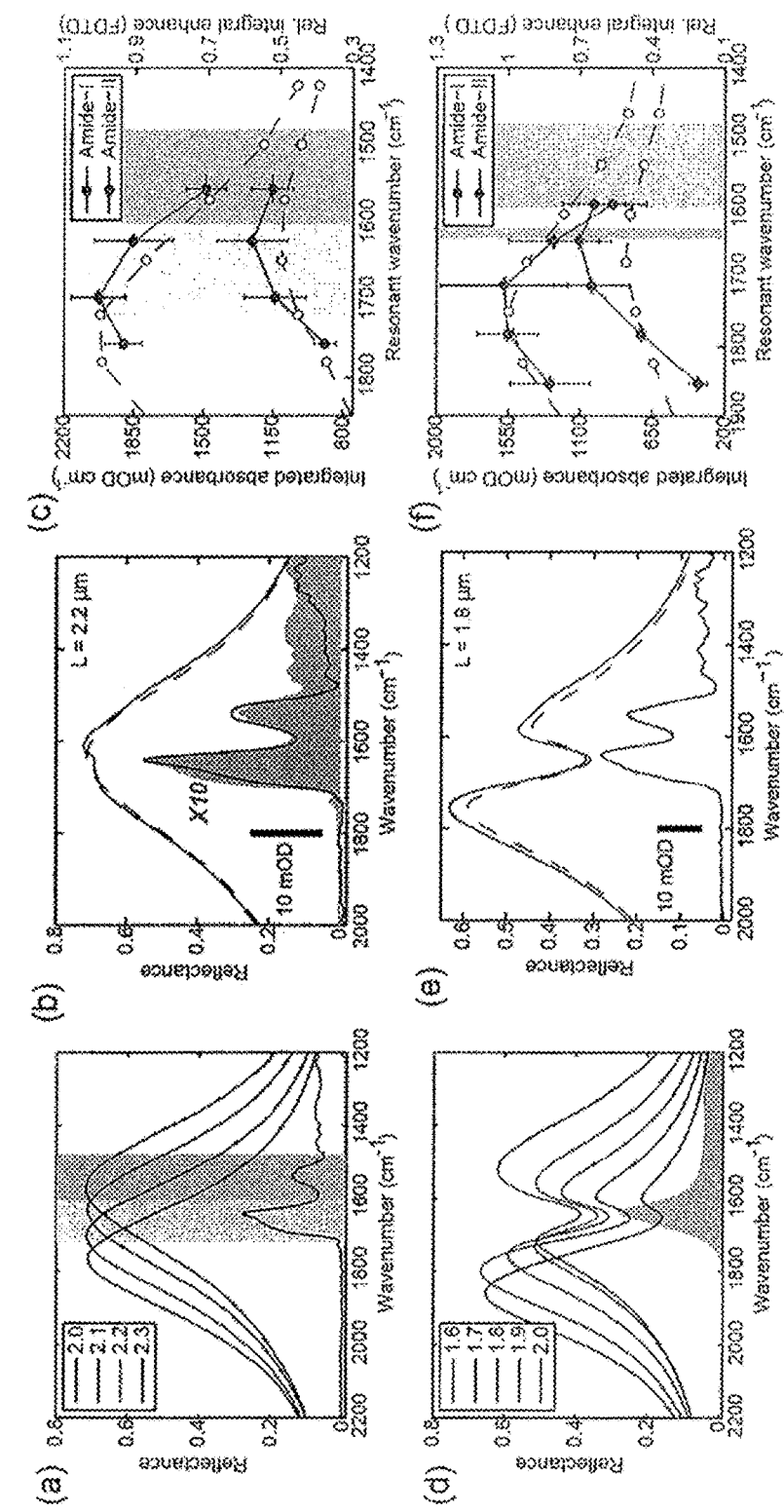

FIG. 4 shows PIR-SEIRA spectroscopy of a protein monolayer in dry and aqueous media. FIG. 4(a) shows reflectance spectra measured for a set of nanoantenna arrays with different lengths as indicated in the legend. The spectral regions associated with the protein amide-I and II bands are indicated by the blue- and red-shaded regions, respectively. Protein spectra (taken via IRRAS) is displayed at the bottom of the figure (a.u.). FIG. 4(b) shows reflectance spectra before (dashed) and after (solid) SA binding for the L=2.2 μm antenna array. The absorbance (see equation 2) is displayed at the bottom of the panel (solid blue line) with units indicated by the scale bar. For reference, a scaled (×10) IRRAS absorbance spectra is displayed as the grey-shaded region. FIG. 4(c) shows absorbance peak integral as a function of the nanoantenna resonance frequency (closed markers and solid lines; left y axis). Markers and error bars indicate averages and ±1 s.d. for N=3 samples. The open markers and dashed lines show the normalized FDTD-simulated intensity enhancement, scaled by relative oscillator strength of the given band (plotted against the right y axis). FIGS. 4(d-e) are analogous to FIGS. 4a-c, but for sampling in an aqueous media (data in f are for N=2 samples). In FIG. 4d, the grey-shaded region shows the ATR spectra of liquid water (a.u.). The grey vertical bar in f indicates $v_{H2O}$ for the bending mode. Note the error bars in both y and x in panels c,f. The former are indicative of overall variability (which includes, for example, surface chemistry effects), whereas the latter show the variation in the plasmonic resonance, and thus point to the highly repeatable nature of infrared antenna devices by standard electron beam lithography.

SEIRA spectroscopy measurements are shown in FIG. 4b. The dashed and solid curves show the reflectance signal after BAT functionalization and SA binding respectively. Obvious dips associated with the amide bands are observable even in these raw spectra. The SA absorbance signal computed from the two (i.e. referenced to BAT), $$A_{SA/BAT} = -\log_{10}(R_{SA}/R_{BAT}) \quad (2)$$

is shown at the bottom of the figure (scale bare is 10 mOD). The curve shown has been corrected for a baseline that results from the slight red-shifting of the plasmonic resonance in response to the non-resonant, high frequency (n=~1.45) component of the refractive index of the protein layer (see FIG. 8). The IRRAS measured absorbance (multiplied by a factor of 10) is shown as the grey shaded region. The exquisite sensitivity of the SEIRA measurement is evident, especially when one considers that a significantly smaller number of molecules and physical area are probed. Quantitatively the peak signal for the amide-I band of 33 mOD is what would be obtained from a 325 nm through a traditional Beer's law transmission measurement. Notably, in contrast to a transmission measurement through a continuous film, the signal from our PIR sample is due to a small quantity of molecules located in the mode volume at the tips of the nano-rod antennas. Scaling for this reduced area fraction by assuming the signal to originate solely these regions, we calculate an E-field-intensity enhancement factor (EF) of 13,800. Significantly, what is actually measured in SEIRA measurements with resonant antennas is not directly absorption, but rather a perturbation of the scattering spectra resulting from coupling to a molecular resonance. Resonant scattering effects have recently been examined using near-field amplitude and phase measurements, indicating that the scattered signal may contain components that vary as the fourth (as opposed to second) power of the E-field. Their implications are significant for our measurements, where explicitly back-scattered light is measured. This is also in accordance with the consistent observation of EFs that are either surprisingly close to or actually larger than the FDTD simulated intensity enhancement here and in other studies.

FIG. 4c examines the variation in this signal amplitude with the detuning of the plasmonic resonance from the frequency of the protein amide bands. Fundamentally, this explores the link between E-field enhancement and our SEIRA signal. On the practical side, this provides a measure of the bandwidth of the system and the range of frequencies that could be monitored. To assess these features, the integrated absorbance over the amide-I and II bands are calculated for the four nano-rod lengths and displayed as a function of the antennas' (far-field) resonance frequency. The data show average values and standard deviations for three sets of measurements using different PIR chips and additionally point to the highly reproducible nature of the plasmonic resonances supported by our engineered nanoantennas (see especially error bars in x). Similarly, we performed FDTD simulations for a set of different rod lengths and computed the average enhancement over a range of frequencies corresponding to a given absorption band (e.g. amide-I or II). These were then scaled to account for the different intrinsic oscillator strengths associated with the two bands and normalized to a maximum value of 1. Firstly, we observe a general correspondence between the trends for experiment and from FDTD predictions, while subtle effects such as the slightly sharper experimental curves are indicative of the aforementioned resonant scattering effects. Secondly, both simulation and experiment point to a promising bandwidth. The plasmonic resonance can be detuned ~300 cm$^{-1}$ before the signal level drops below 75% of the max, indicating that a single antenna design could probe a fairly broad range.

That similar measurements can readily be performed in solution using the PIR chip is demonstrated in FIGS. 4d-f. The effect of the water vibrational band is clearly visible in the plasmonic reflectance spectra (gray shaded region displays an ATR measured spectrum from water for reference). Though the plasmonic substrates confine the E-field to within ~80 nm of the surface, the ~20% modulation in reflectance due to the water band points to the significant SEIRA enhancement. Critically, however, a 5 nm thick protein monolayer bound to the nanoantenna surface represents a far greater fraction of this path than it would for a traditional transmission measurement. Thus, as shown in FIG. 4e, high quality spectra can readily be obtained for molecules in an aqueous environment. The slight reduction in signal results from the increased damping of the plasmonic resonance due to the water band, corroborated by the variations in FIG. 4f. Yet, the 22 mOD signal is still significant, corresponding to an EF of 7,700 and, significantly, over an order of magnitude increase over what would be measured via ATR sampling (see FIG. 9).

Finally, we emphasize the extremely high SNR evident in our measurements. Comparing the IRRAS measurement with our SEIRA spectra, the SNR are found to be comparable. This is significant given that our PIR signal comes from only a 100×100 µm² region, which represents a 3,000 fold reduction in sample area compared with IRRAS. Further improvements in the SEIRA SNR should be straightforward, e.g. by utilizing a polarization intensive antenna. Our PIR platform thus offers significant advantages over the state of the art IR techniques, effectively overcoming the significant complications in measuring protein monolayers in aqueous environments, while introducing a level of compactness and versatility previously absent.

Figure 5:
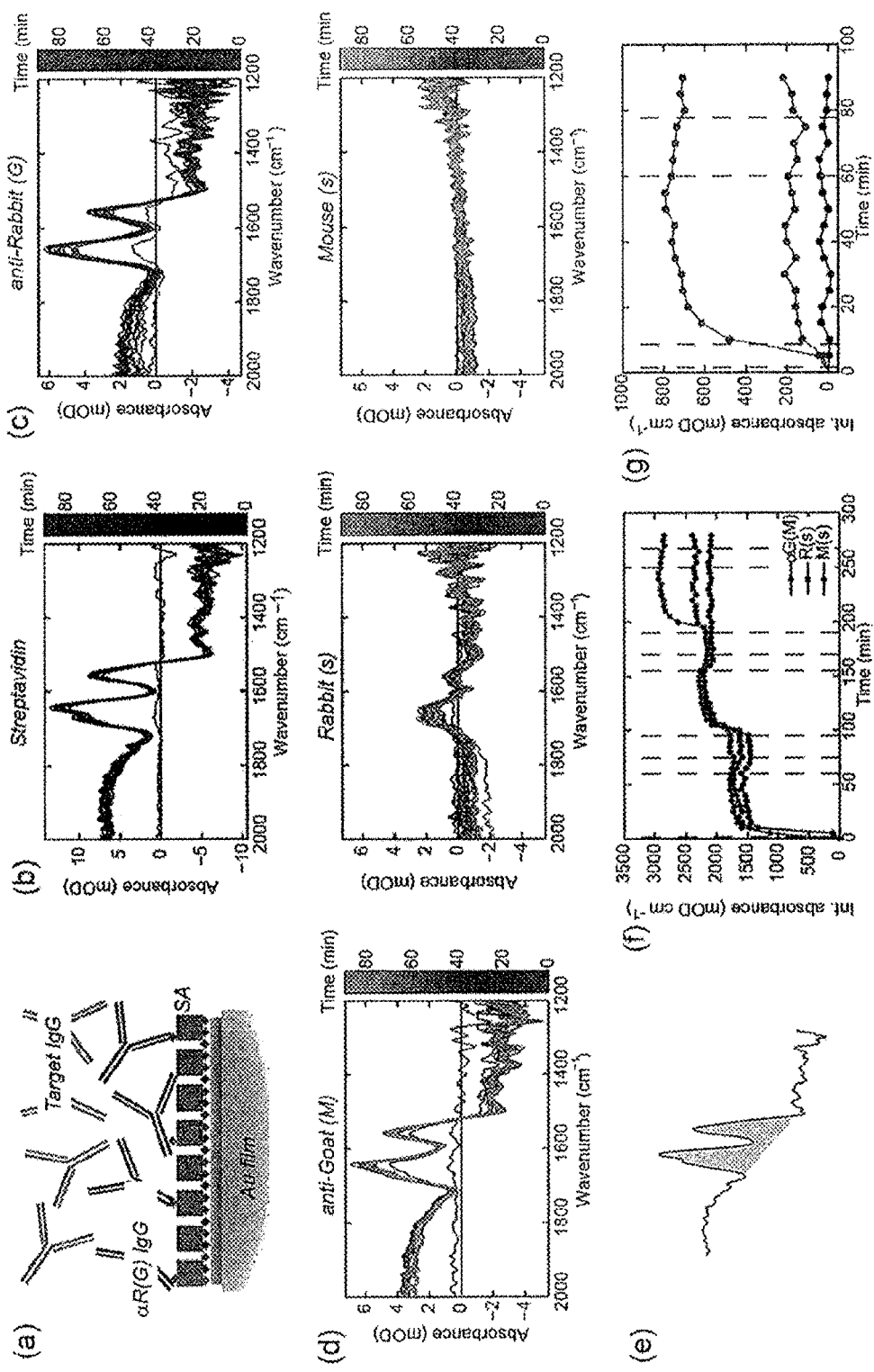

FIG. 5 illustrates multiple protein binding monitored in-situ with PIR-SEIRA. FIG. 5(a) is a schematic of protein-binding interactions measured. FIGS. 5(b-d) shows a time series of spectra taken during (b) SA, (c) (b)aR(G) and (d) three target IgG-binding steps. FIG. 5(e) shows amide band peak integral used to assess protein binding. FIG. 5(f) shows peak integral (integrated absorbance) evolution over time during the protein-binding measurements for the three samples.

FIG. 5(g) shows an expansion of the incremental change during the three different target IgG-binding step.

In-Situ Protein Immuno-Assays via Chemical Fingerprints: The ability of our PIR technology to operate in aqueous environments at high sensitivity and SNR is ideally suited to time-resolved studies of biomolecules and other chemical species at the monolayer level. We demonstrate this application by monitoring a series of biologically relevant protein-protein binding events as well as chemically distinct model substances. The latter set of measurements is notable given that refractive-index sensors probe only mass accumulation and are thus incapable of performing a distinction that, as will be shown, is straightforward with our IR measurements.

We first performed 3 assays each consisting of three proteins. The PIR chips were inserted into the flow cell following BAT functionalization. Spectra were recorded at 5 min intervals as the various buffers and protein solutions were introduced. On the basis of the considerations detailed in FIG. 4f, we monitored the L=1.8 µm array throughout.

The protein interactions studied are shown schematically in FIG. 5a. The three assays shown were performed in series, one after the other using different PIR chips (albeit containing nominally identical sets of plasmonic arrays). All three experiments are identical in their first two steps, which consist of SA followed by a biotin labeled anti-rabbit (goat host) ($^{(b)}$aR(G)) IgG. For the third step, a target IgG intended to interact with the immobilized $^{(b)}$aR(G) is introduced. This IgG is varied between the three experiments to provide different levels of binding. Specifically, anti-goat (mouse host) (aG(M)), rabbit IgG (from serum) (R(S)) and mouse IgG (from serum) (M(s)) were chosen to provide high, weak and zero specific binding to the immobilized $^{(b)}$aR(G). These are estimated to correspond to, high (≥1); weak (likely ~⅓); and zero bound target per immobilized $^{(b)}$aR(G). In all experiments, for each step the protein solution is introduced at a concentration of 50 g/mL and allowed to flow for 1 h. Each step is followed by a 15 min rinse with a detergent, then pure buffer.

Differential absorbance spectra at each time are plotted in FIGS. 5b-d. For each step, the absorption is referenced to the spectra taken immediately before the given protein solution is introduced. Each set of spectra therefore give the increase in absorption due solely to the binding of the protein associated with the given step. Due to the relatively low dielectric constant contrast between the bound protein and water (as compared to air) and the fact that we monitor a single nanoantenna array throughout, it was not necessary to perform the baseline correction used in conjunction with FIG. 4. As a result, we observe the progression of a slowly varying step-like feature in our spectra associated with a shift in our plasmonic resonance as material binds. Focusing on the specific protein absorption bands, for the three different target IgG steps, shown in FIG. 5d, we observe significant increase in the amide-band absorption for the aG(M), much smaller signals from R(s) and apparently no binding from the M(s) IgG. These observations can be summarized and displayed in a more quantitative fashion by computing the peak integrals as a function of time, as shown in FIG. 5e-g. The number of amide bonds corresponds to the number of amino acids in a protein, hence the integral over the total amide-I and II peak region (FIG. 5e) serves as a proxy for protein accumulation. The resulting binding curves in FIG. 5f,g are qualitatively similar to those that can be obtained with refractive index sensors and also quantitative in nature. For the first two steps, the three experiments show excellent agreement, highlighting the high degree of repeatability of our measurements. For the target IgG step, shown in detail in FIG. 5g, the varying degrees of binding are evident, with roughly ⅓-¼ the amount of R(s) compared to aG(M). Importantly, despite the similarity of the appearance of these results to those of label-free sensors, the signal here corresponds directly to the number of amide-bonds present. It is therefore specific to the chemical structure of the bound molecules as opposed to non-specific mass accumulation.

Identification and Tracking of Chemically Distinct Substances: We highlight this key ability of IR spectroscopy to measure molecular bond specific fingerprints and demonstrate the implied capability to distinguish and track chemically distinct substances in FIG. 6. Binding interactions as in FIG. 5 are monitored. The experiment consists of two binding steps, SA followed by biotin labeled latex beads ($^{(b)}$LB), shown in FIG. 6a. While both the protein and beads have similar refractive indices in the visible/near-IR, their different molecular structure is immediately apparent in the spectra shown in FIGS. 6b,c. Styrene contains no amide bonds, hence the characteristic absorption peaks associated with the protein binding are entirely absent in the $^{(b)}$LB spectra shown in FIG. 6c. Instead, two narrow bands at ~1490 and ~1450 cm$^{-1}$ appear. These can be assigned to vibrational modes associated with the benzene ring in the styrene molecule, shown in FIG. 6d. An additional feature of note is the broad negative peak, corresponding to a reduction in absorption, at ~1650 cm$^{-1}$. We assign this feature to the OH bend vibration of liquid water and propose that it results from its displacement as the beads bind at the nano particle surface. Such effects are likely not observed during the protein binding steps due to the fact that proteins are essentially highly flexible folded strands that can interact with and internalize a significant amount of water molecules. Therefore, in contrast to the beads, they can be thought of as extremely porous and do not displace water to the same degree.

The chemically distinct substances monitored here thus consist of protein, liquid water and polystyrene. The characteristic peak integrals and associated molecular vibrations are shown in FIG. 6d. Both the amide-I and II are monitored separately, as the amide-I overlaps with the OH bend, which also varies over the course of the measurements. The ability to sensitively chart the movement of the various chemical groups, shown in FIG. 6e,f adds a clear extra dimension to IR spectroscopy with our plasmonic technique, not present in traditional label free techniques. The ability to monitor such subtle effects as the displacement of minute quantities of water molecules further highlights the level of information that can be obtained on trace samples via PIR measurements.

Figure 6:
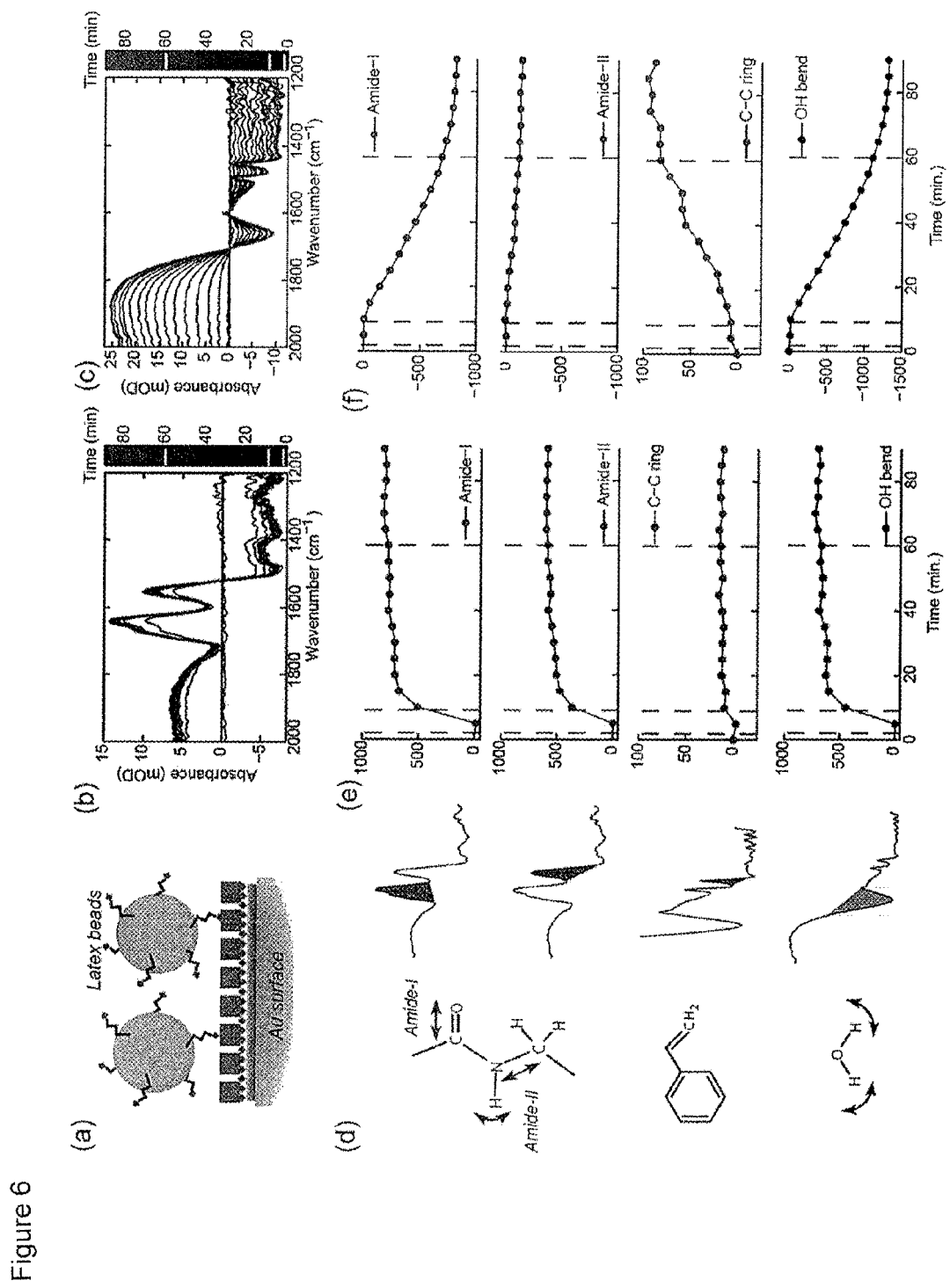

FIG. 6 illustrates a molecular bond-specific signatures of bound particles. FIG. 6(a) is a schematic of the latex bead-SA binding. FIG. 6(b,c) illustrates time-series absorbance spectra during the SA- and (b) LB-binding steps. FIG. 6(d) shows specific chemical structures and their corresponding infrared fingerprints (peak integrals) used to monitor their presence during the flow experiments. FIGS. 6(e,f) illustrates the evolution of the peak integrals (integrated absorbance, units of mOD cm$^{-1}$) over time during SA- and (b) LB-binding steps, respectively.

With the proposed PIR technique according to the present invention and its usage to detect and chemically identify the constituents in binding interactions, we demonstrate a highly sensitive, compact, and versatile chip-based platform for in-situ IR absorption spectroscopy. The high quality data with large SNR, imply the opportunity for detailed IR studies down to the single molecule level. Significantly, beyond the chemical identification capability demonstrated here, the extension of this system to monitoring conformational changes that do not result from mass accumulation, and are therefore largely invisible to RI sensors, should be possible. The ability to perform such measurements in situ, on monolayer thickness samples enables studies involving direct electron transfer, such as redox reactions, as well as the investigation of important interface effects.

Our reliance on engineered plasmonic nanoantennas allows for highly repeatable measurements, well defined detection volumes and large enhancement factors, as demonstrated in FIG. 4. Furthermore, it allows for the large body of research on plasmonic nano particle design to be put to use, in order to deterministically tailor resonance properties as desired for a given experiment. Finally, the ability to efficiently re-direct far-field radiation in the manner implemented here is unique to engineered nanoantennas and critical to our chip-based design that eliminates the need for bulky high index ATR crystals and their associated coupling optics. Recent work on directional plasmonic antennas can be used to optimize or find new functionalities related to this feature as well.

Our measurements here, performed in an IR microscope with a single element detector, provide a demonstration of the capabilities and convenience of our PIR technique. Furthermore, In conjunction with IR imaging detectors and bright QCL sources, PIR can enable a number of possibilities in examining chemical heterogeneity and increasing throughput of measurements. In combining dramatic signal amplification with a non-classical internal reflectance mechanism, our platform enables IR absorption spectroscopy to be performed on monolayer thickness samples with unparalleled sensitivity in a chip-based platform. This provides a new class of IR absorption sensors and spectroscopy tools as well as a new community from e.g. nano-photonics, microfluidics and other backgrounds to take advantage of their immense potential.

Numerical Calculations: Numerical (FDTD) simulations were performed using a commercial software package (Lumerical). Periodic boundary conditions were used throughout with excitation due to a normally incident plane wave entering the simulation domain from the substrate side (see FIG. 1f). The dielectric constants of Au and $H_2O$ were taken from Palik 1988. A thin (5 nm) chromium (Cr) adhesion layer, present in the fabricated samples, was omitted from the simulations. A local mesh with spacing $\delta=1$ nm in a region about the tip ends of the rods was used.

The average E-field intensity enhancement over a given frequency band (amide-I or II) was computed from FDTD simulations via $F(\nu_1, \nu_2)=\int_{\nu_1}^{\nu_2}<|E/E_0|^2>d\nu/(\nu_2-\nu_1)$, where $<|E/E_0|^2>$ denotes a spatial average over the volume defined in FIG. 1e. Thus $F_I=F(1600$ cm$^{-1}$, $1720$ cm$^{-1})$ and $F_{II}=F(1500$ cm$^{-1}$, $1600$ cm$^{-1})$ were obtained as functions of the nanoantenna array resonance frequency for the amide-I and II bands respectively. To account for the different intrinsic oscillator strengths associated with the two protein bands, we scaled $F_{II}$ by the ratio of the amide-II to amide-I band integrated absorbance obtained from the IRRAS data (for which enhancement varies negligibly with frequency). Finally, to compare the trends in the field enhancement with the experimental data, $F_I$ and the scaled $F_{II}$ were normalized to a maximum value of max($F_I$)=1 for the dry and aqueous environment measurement sets.

Sample fabrication: example samples were fabricated via electron beam lithography and lift-off on CaF$_2$ windows (13 mm diameter; 1 mm thick). Particles are formed by depositing a 5 nm thick Cr adhesion layer followed by 100 nm of Au via electron beam evaporation. Following lift-off an O$_2$ plasma clean was used to remove any small residual amount of PMMA. Samples were stored under vacuum prior to use. Gold slides for IRRAS measurements were prepared in-house through evaporation of Cr/Au (identically to the particles) on polished silicon.

Spectroscopic measurements: FTIR measurements were performed on a Bruker IFS 66/s spectrometer using a Mercury Cadmium Telluride (MCT) detector. All data were taken under identical acquisition settings: a mirror velocity of 40 kHz, 512 scans co-added and 8 cm$^{-1}$ resolution. Reflectance measurements are referenced to an Au mirror. SEIRA measurements were performed with an IR microscope (Hyperion 1000, Bruker) with a 0.4 NA, 15× objective. Knife edge apertures limited the collected signal to a single 100×100 µm$^2$ array for each measurement. A plastic enclosure was purged with dry and CO$_2$ filtered air to limit interference from water vapor lines. Typically reference water vapor spectra were recorded and used to subtract out any residual lines.

Grazing angle (80 deg. from the surface normal) IRRAS measurements were performed to characterize the SA protein absorbance. Samples of ~1×1 in were used and placed on a mask that limited the sampling area to about 6 mm in diameter. Notably, since samples are also formed on Au slides, not only can identical preparation techniques be used, but the sample is probed by the E-field oriented perpendicular to the Au surface, just as in SEIRA, hence the same component of the sample dielectric function is measured. ATR measurements were performed using a single reflection accessory, with spectra ratio-ed to a background spectra recorded from the bare crystal.

In addition to the IRRAS reference measurements, two sets of control measurements were performed. In the first, samples were fabricated and measured such that the nanoantenna resonances were scanned over a wide range of wavelengths and show the characteristic Fano-lineshapes and eventual decay in amplitude of the amide bands and the antenna resonances are detuned (see FIG. 10). In the second, measurements were performed with light polarized perpendicular to the antenna long axis such that no resonances were excited and show, as a consequence, no amide band features (see FIG. 11). Both were performed in dry and aqueous environments.

For the SEIRA measurements in an aqueous environment, an exemplary small fluidic chamber was constructed out of poly-methyle di-siloxane (PDMS). In this case, the chamber was irreversibly sealed at its bottom to a glass microscope slide by $O_2$ plasma oxidation and Si—OH bonding. The $CaF_2$ sample was pressure sealed to form the top window of the fluidic cell as shown in FIG. 3.

The volume of the chamber was approximately 0.5 mL, measured by filling with a syringe pump. For static measurements (FIG. 4), the chamber was filled with PBS and the inlet and outlets were sealed to prevent flow. During binding measurements (FIGS. 5,6) a constant flow rate of 0.14 mL/min was maintained.

Data processing and analysis: Equation 1 and the modified version (including the OH bend mode) used to extract antenna resonance parameters are derived in the later section entitled 'Supplementary Methods'. The absorbance spectra used to analyze protein and biomolecule binding are determined from reflectance measurements using equation 2. The resultant spectra display absorption bands associated with the SEIRA effect as well as a step-like base-line. This base-line results from the fact that the binding of protein to the surface of the nanoantenna resonators shifts their center frequencies, due to the n~1.45 non-dispersive component of the proteins' refractive index. While polynomial base-line correction is common in IR spectroscopy, we used the physical origin of the feature to constrain the functional form of the fit. The specific function used and fitting procedure are set out in the later section entitled 'Supplementary Methods'.

The SEIRA enhancement was quantified in terms of an effective path length ($d_e$), enhancement factor (EF) as well as comparison with ATR. These all began with our IRRAS measurements, from which the expected transmission signal from an ideal Beer's law measurement was determined via the relation $$\Delta T \approx \frac{n_\infty^3}{4} \frac{\cos\theta}{\sin^2\theta} \Delta R_{IRRAS} \quad (3)$$

The high frequency protein refractive index, $n_\infty=1.48$ is determined from a fit (equation 4 below) and $\theta=80°$ is the incident angle in the IRRAS measurements. The 3.01 mOD for IRRAS correspond to 0.44 mOD from equation 3. For a thin film, the effective path length is then $d_e \approx d(\Delta R/\Delta T)$, where $\Delta R$ is the change in reflectance from the SEIRA measurement and $\Delta T$ is given by equation 3 (derivation in section 'Supplementary Methods'). The enhancement factor is the signal enhancement, scaled to account for the reduced area fraction as, $EF=(\Delta R/\Delta T)/A$, where $A=2$ wt/$P^2$ is the area fraction (w=200 nm, t=100 nm being the nominal rod width and thickness respectively) of the unit cell occupied by the (two) rod tips.

Figure 9:
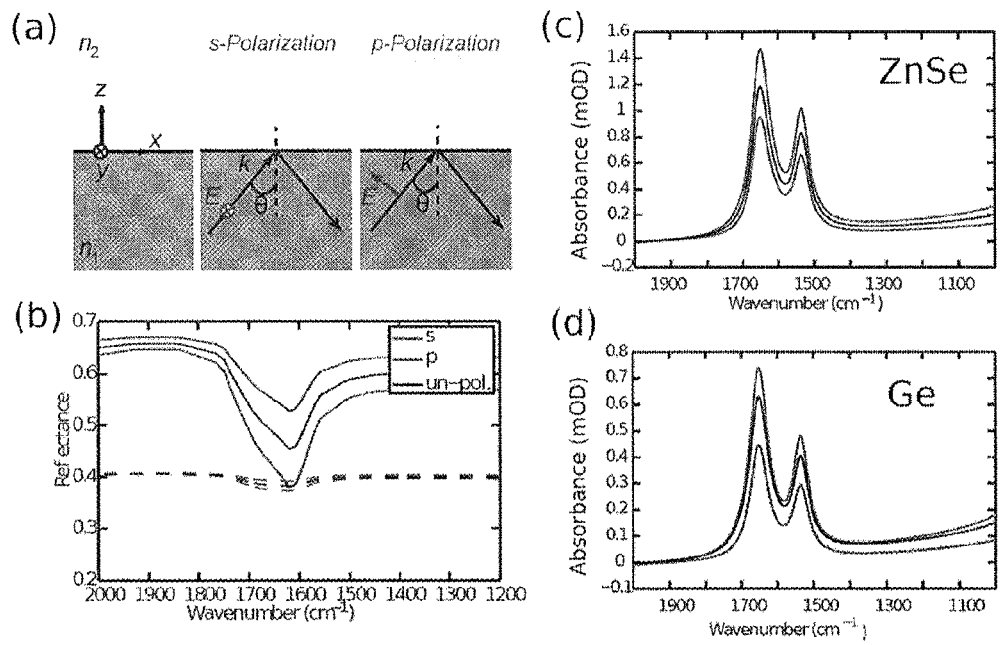

Comparison with ATR was accomplished by calculating the expected signal for an ATR measurement from the Fresnel equations (see FIG. 9). Here the SA dielectric function was approximated by fitting IRRAS data with a two oscillator dielectric function, $$\varepsilon(\omega) = (n_\infty)^2 + \frac{S_I}{\omega_I^2 - \omega^2 - j\omega\gamma_I} + \frac{S_{II}}{\omega_{II}^2 - \omega^2 - j\omega\gamma_{II}} \quad (4)$$

for the amide-I and II bands. For the amide-I band, the calculated absorbance for ATR was determined to be 1-1.4 mOD (0.4-0.7 mOD) for ZnSe (Ge) elements respectively. Both show similar overall throughput (see FIG. 9) to our PIR method.

Peak-to-peak and rms noise levels were determined or both the IRRAS and SEIRA absorbance, evaluated over the standard 2000-2200 $cm^{-1}$ mid-IR window. This noise value was scaled for the nanoantenna measurements to account for the fact that the window lies at the edge of the reflectance peak. Peak-to-peak (rms) values of 160 (680), 80 (310) and 110 (480) SNRs were thus determined for the dry and aqueous environment SEIRA and IRRAS measurements respectively.

Peak integrals comparing chemical bands' signatures were computed via $P(v_1, v_2)=\int_{v_1}^{v_2}(A_{k,j}-h)\,dv$, for the amide-I, II, combined amide-I and II, $H_2O$ and CC regions as shown in FIGS. 4-6. The parameter h is a reference line connecting two selected points ($v_1$ and $v_2$), i.e. $h=m(v-v_{h1})-A_{k,j}(v_{h1})$ where $m=(A_{k,j}(v_{h1})-A_{k,j}(v_{h2}))/(v_{h2}-v_{h1})$ is the slope (see Supplementary Table S1 below). Since the refractive index contrast between protein and water is small (relative to protein and air) and our binding measurements used a single plasmonic structure, the linear reference line was sufficient for analysis of the data in FIGS. 5 and 6 without the aforementioned constrained base-line correction.

| Band | $[v_1, v_2]$ | $[v_{h1}, v_{h2}]$ | Main text FIG. |
|---|---|---|---|
| Amide-I | [1600, 1720] | [1480, 1720] | FIG. 4 |
| Amide-II | [1500, 1600] | [1480, 1720] | FIG. 4 |
| Amide-I, II | [1500, 1720] | [1480, 1720] | FIG. 5 |
| Amide-I (2) | [1600, 1720] | [1600, 1720] | FIG. 6 |
| Amide-II (2) | [1500, 1600] | [1500, 1600] | FIG. 6 |
| C—C Ring | [1435, 1481] | [1435, 1481] | FIG. 6 |
| O—H Bend | [1600, 1750] | [1600, 1750] | FIG. 6 |

Supplementary Table S1: Peak integral definitions and parameters. The values $[v_1, v_2]$ denote the frequencies (in $cm^{-1}$) over which the peak integral is performed. The values $[v_{h1}, v_{h2}]$ give the frequencies ($cm^{-1}$) used to construct the reference line has described above.

Surface chemistry and binding protocols: The formation of the BAT (CMT015-25, nano-Science instruments), SAM on our Au nanoantennas was accomplished by incubating samples in an 0.5 mM ethanol based solution overnight.

Streptavidin (SA) (21125, Pierce) was attached, either by spotting (~20 μL volume spot) and incubating for 1 h as in the case of the static measurements (FIG. 4), or by circulating the solution in a flow cell as in the time resolved measurements (FIGS. 5-6). In either case, a 50 μg/mL solution in PBS was used. Spotted samples were rinsed in PBS with detergent (tween 20) (PBST) for 5 min, followed by pure PBS and Millipore water, 5 min each. The flow experiments followed a similar rinsing procedure, consisting of 15 min of PBST followed by 15 min of PBS.

For the immuno-assays, IgG samples were selected based on their recognition and host properties (see below section 'Supplementary Methods'). All were used at concentrations of 50 μg/mL diluted in PBS. Given the low intensity on the sample of the Globar source used in the experiments, protein de-naturing due to thermal effects was not a concern (see section 'Supplementary Methods').

For the beads experiments, biotin labeled latex beads with a mean size of 250 nm were used (L7655, Sigma). The solution was diluted to 0.01% solids (weight/weight) in PBST corresponding to $1.2 \times 10^{10}$ particles per mL (50 pM).

SPR measurements were performed on an immuno-assay to check binding kinetics and the deposited surface density of the SA layer (see FIG. 12). Measurements were performed on a Biacore 3000 using Au chips functionalized with BAT as in the FTIR measurements. A response of 1750 RU was measured for SA, corresponding to a surface concentration of ~175 ng/cm$^2$ (1 RU=1 pg/mm$^2$ for proteins (GEHealthcare), in close agreement with the value of ~200 ng/cm$^2$ in literature.

Figure 7:
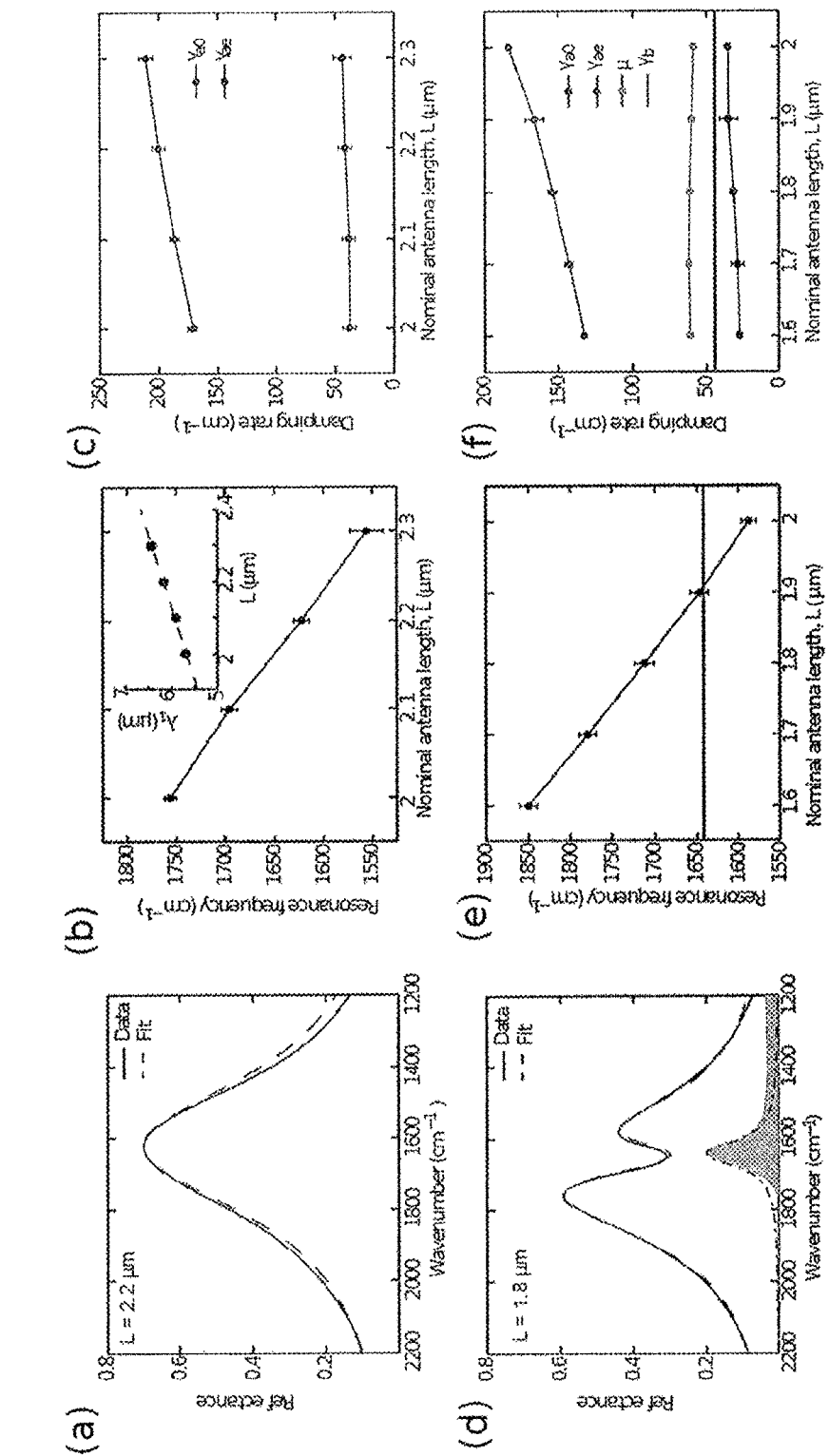

Supplementary Methods:

FIG. 7 shows experimental characterization of linear mid-IR nano-antennas for PIR spectroscopy. FIGS. 7(a-c) show antenna resonances in dry environment. Measurements are taken from 4 arrays, with nominal lengths varied between 2.0 and 2.3 μm while the periodicity is P=2.75 μm (square lattice) (a) Measured reflectance data for a L=2.2 μm antenna array and TCMT fit corresponding to the m=1 resonance. (f) Variation in resonance frequency with nominal antenna length. The inset shows the linear fit to the resonant wavelength: $\lambda = c_1 L + c_0$. The fit gives $c_1$=2.47, $c_0$=0: 95 with an r$^2$ of 0.997. (g) Radiative ($\gamma_{ae}$) and non-radiative ($\gamma_{a0}$) damping rates extracted from simulated reflectance spectra as a function of nano-antenna length. (h-j) Measured reflectance spectra, TCMT fit and extracted resonance frequencies and damping rates for nano-antennas in an aqueous environment. Measurements are taken from 5 arrays, with nominal antenna lengths varied between 1.6 and 2.0 μm and fixed periodicity (P=2.5 μm, square lattice). In the fits $v_b$ and $\gamma_b$ are fixed while $v_a$, $\gamma_{ae}$, $\gamma_{a0}$ and μ are let to vary. (h) Reflectance spectra and fit for a L=1.8 μm antenna array (P=2.5 μm period). The dash-dotted line shows the resonance line-shape of the OH band and its correspondence to the experimentally measured H$_2$O absorption (grey shaded region). (i) Extracted antenna resonance frequency. (j) Extracted antenna damping rates and antenna-OH bend coupling parameter. Points and error bars in (e,f) and (h,i) correspond to average values and ±1 standard deviation for N=3 and N=2 samples respectively. The (fixed) values of $v_b$ and $\gamma_b$ are indicated by the red lines in (i) and (j) respectively.

Figure 8:
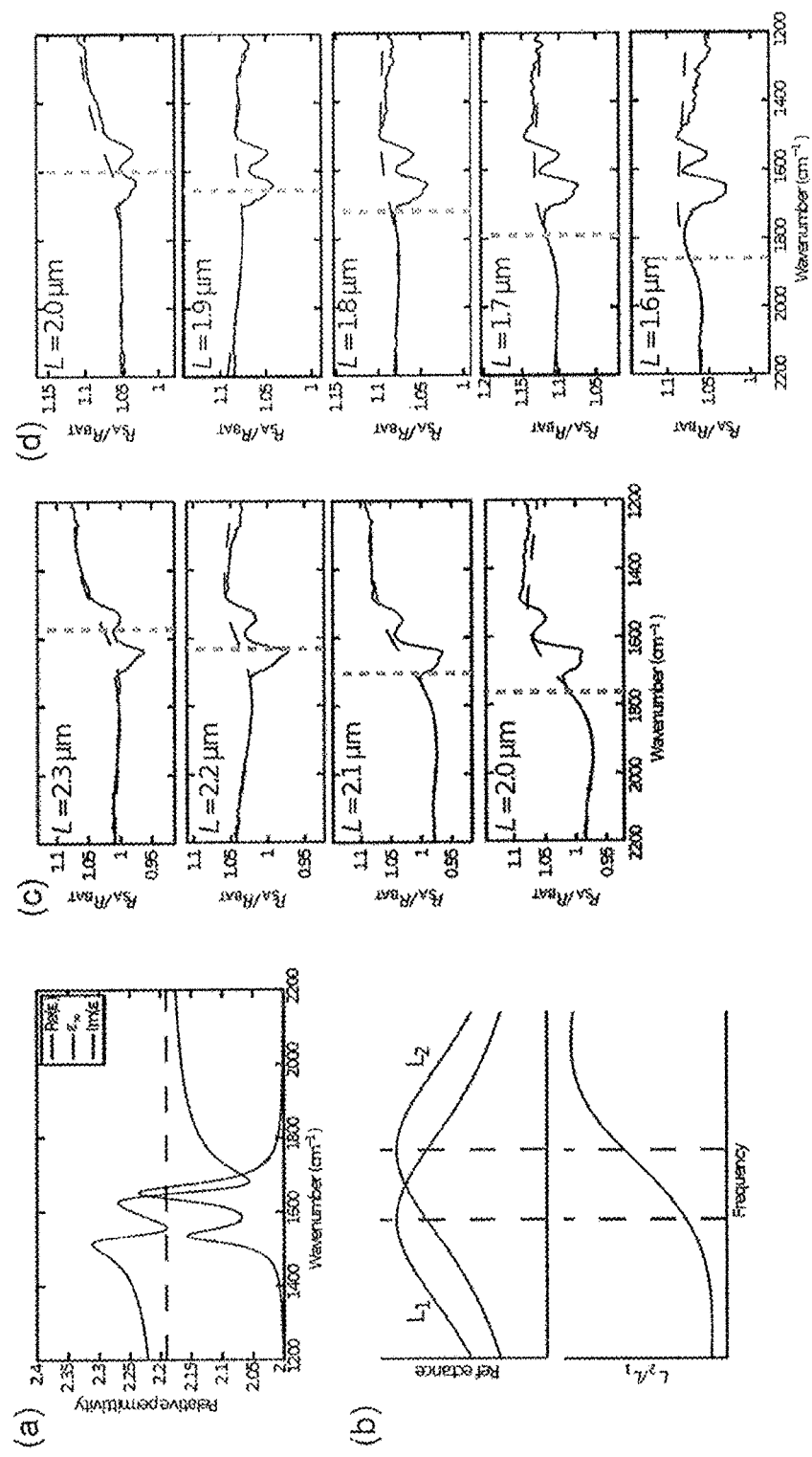

FIG. 8 shows constrained base-line correction based on a peak shift. FIG. 8(a) shows the complex dielectric function of a sample in the IR can be approximated as being comprised of a non-resonant, high-frequency constant background and resonant terms corresponding to the vibrational modes in the sample. Real and imaginary parts of the extracted dielectric function of a protein (SA) are shown in blue and red respectively. The high-frequency, non-resonant term ($\epsilon_\infty = n^2_\infty$) is shown as the dashed black line. (b) The peak-shift induced by the non-resonant term causes a step-like base-line in data when the reflectance of an array with protein is ratio-ed to one without to calculate the differential absorbance. (c-d) A base-line function defined as the ratio of two Lorentzian peaks can be fit to the experimental data. The black curves show the quantity $R_{SA}=R_{BAT}$, i.e. the reflectance of a nano-antenna array coated with SA divided by the reflectance from the same array, without the SA, as described in equation (2). The red dashed lines show the fitted base-line. Performing the fit on the reflectance ratio as opposed to absorbance was more intuitive. The dashed vertical grey line indicates the position of the antenna resonance, before SA binding. Data and fits in dry (c) and aqueous (d) environments are shown.

FIG. 9 shows calculated quantities of interest for comparison with ATR sampling. In FIG. 9(a) All ATR calculations are performed based on the standard solutions to Maxwell's equations in a 1D layered system. The coordinates and polarization conventions used are shown. Calculations are performed for ZnSe and Ge crystals, which have refractive indices of n=2.4 and n=4.0 respectively. (b) Throughput of ATR crystals in the vicinity of the water OH bend mode. Solid lines: ZnSe crystal. Dashed lines: Ge crystal. Angle of incidence for both is 40 degrees. It was assumed that light entered the crystal at normal incidence, hence the base-line reflectance corresponds to $(1-R_0)^2$ where $R_0$ is the reflectance at 0° from the prism-air interface calculated from the Fresnel equations. The dip at ~1650 cm$^{-1}$ is from water absorption, which is larger for ZnSe due to its much greater penetration depth (see, e.g. FIG. 1d). (c,h) Absorbance signals from an ATR measurement of SA in water, using ZnSe (panel c) and Ge (panel d) crystals. Curves are shown for s, p and un-polarized light.

Figure 10:
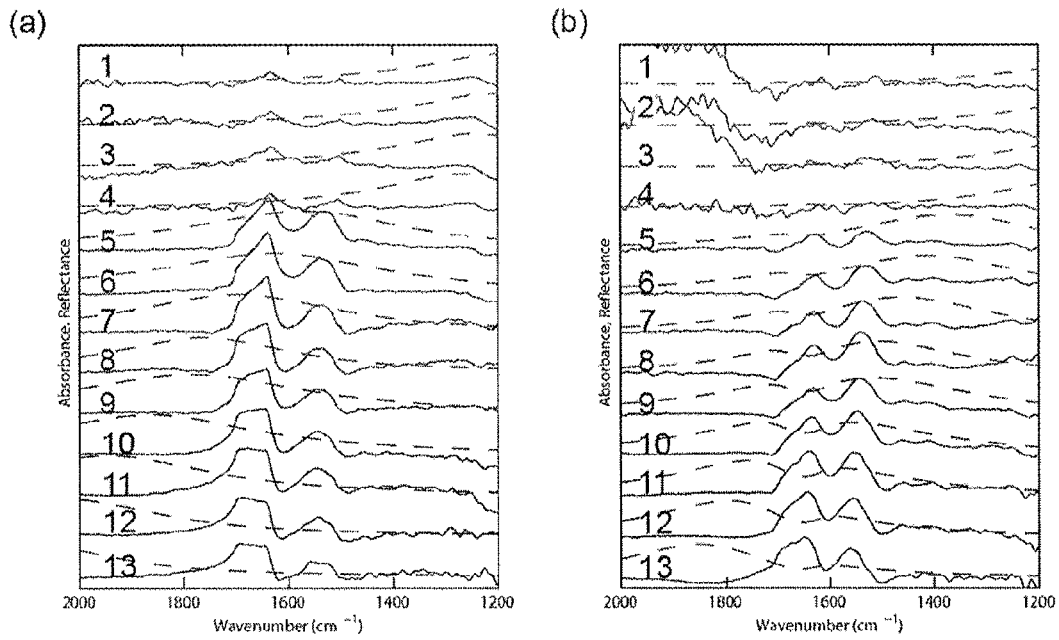

FIG. 10 shows an expanded set of measurements scanning the plasmonic resonance wavelength through the protein amide-I and II absorption bands' frequencies. Curves are arranged in order of decreasing nano-antenna length (decreasing resonant wavelength) with curve 1 having a length of 3.2 μm and curve 13 corresponding to a 1.6 μm long antenna. Arrays 1-4 have lengths ranging from 3.2-2.9 μm, increments of 100 nm, and a period of 3 μm. Arrays 5-8 have lengths ranging from 2.3-2.0 μm. Arrays 9-13 have lengths ranging from 2.0-1.6 μm. Absorbance curves are displayed as the solid lines, while the corresponding bare array reflectance spectra are overlaid as the dashed lines for reference. (a) Dry environment. (b) Aqueous environment. The step-like feature in (b), observed around ~2000 cm$^{-1}$ for curves 1-3, is associated with the red-shifting of the higher order, m=3 antenna like mode of the plasmonic resonators due to the local refractive index change upon binding of the protein.

FIG. 11 shows measurements taken with 's-polarization' (perpendicular to the nano-rod long axis). (a) Dry environment, bare structures. (b) Aqueous environment, bare structures. (c) Dry environment, SA coated structures. (d) Aqueous environment, SA coated structures. The primary, consistent feature in (b,d) is associated with the water band. A very slight signal from the plasmonic structure can also be observed as a result of slight imperfections in the polarizer alignment.

FIG. 12 shows Surface plasmon resonance spectroscopy on a SA monolayer and IgG binding assay. Concentrations and volumes of the injected solutions are indicated in the graph.

Generalized Resonator Model for Plasmonic Nanoantenna in Dry and Aqueous Environments The Temporal Coupled Mode Theory (TCMT) formalism can be applied to the generalized resonator schematic shown in FIG. 2b,c to derive the expression for the reflectance of the bare antenna given by equation (S1) as follows. The coupled mode equations for the configuration are:

$$\frac{da}{dt} = jv_a a - (\gamma_{ae} + \gamma_{a0})a + (\kappa_1 \ \kappa_2)\begin{pmatrix} s_{1+} \\ s_{2+} \end{pmatrix} \quad (S1)$$

$$\begin{pmatrix} s_{1-} \\ s_{2-} \end{pmatrix} = C\begin{pmatrix} s_{1+} \\ s_{2+} \end{pmatrix} + a\begin{pmatrix} \kappa_1 \\ \kappa_2 \end{pmatrix} \quad (S2)$$

In equations (S1) and (S2), a is the mode amplitude, $v_a$ the center frequency, $\gamma_{ae}$ the radiative loss rate and $\gamma_{a0}$ the non-radiative damping rate. The incoming, reflected and transmitted waves are represented by $s_{1+}$, $s_{1-}$ and $s_{2-}$ respectively ($s_{2+}$=0). The traveling wave amplitudes, $s_{(1,2)(+,-)}$ are normalized such that $|s|^2$ is the power carried by the wave. The magnitude squared of the generalized resonator amplitude, $|a|^2$ corresponds to the energy stored in the plasmonic nano-antenna's resonant mode. The coupling constants, $\kappa_1$ and $\kappa_2$ dictate the transfer of energy between external radiation at either of the 2 ports and the resonant mode. Assuming an even symmetry mode, $\kappa_1=\kappa_2=\kappa$ as in the figure (FIG. 2c).

In the absence of the resonator, the incoming and outgoing waves at the two ports are related through the direct transmission and reflection coefficients (r, t), of which the matrix C is comprised, $$C = e^{j\phi}\begin{pmatrix} r & jt \\ jt & r \end{pmatrix} \quad (S3)$$

The direct process matrix, C, coupling $\kappa$ and the external loss rate, $\gamma_{ae}$ are related by time-reversal symmetry and energy conservation considerations. Since the CaF2 substrate reflects <3% of incident light we use, $$C = \begin{pmatrix} 0 & 1 \\ 1 & 0 \end{pmatrix} \quad (S4)$$

which leads to r=0, t=1 and $\phi=-\pi/2$ and $\kappa=\sqrt{\gamma_{ae}}$ Substitution into equations (S1) and (S2) yields, $$R_a = \frac{(\gamma_{ae}^2)}{(v - nu_a)^2 + (\gamma_{a0} + \gamma_{ae})^2} \quad (S5)$$

This approach can readily be extended to include the effects of the OH bend mode by including a second resonator, coupled to the first as indicated schematically in FIG. 2d. In this case, the coupled mode equations become:

$$\frac{da}{dt} = jv_a a - (\gamma_{ae} + \gamma_{a0})a + j\mu b + \begin{pmatrix} \kappa_1 & \kappa_2 \end{pmatrix}\begin{pmatrix} s_{1+} \\ s_{2+} \end{pmatrix} \quad (S6)$$

$$\frac{db}{dt} = jv_b b - \gamma_{b0} b + j\mu a \quad (S7)$$

$$\begin{pmatrix} s_{1-} \\ s_{2-} \end{pmatrix} = C\begin{pmatrix} s_{1+} \\ s_{2+} \end{pmatrix} + a\begin{pmatrix} \kappa_1 \\ \kappa_2 \end{pmatrix} \quad (S8)$$

where in setting $\gamma_{be}=0$ and decoupling resonator b from external radiation we have assumed that the interaction of the absorption band with the plasmonic resonator is significantly stronger than its direct interaction with far-field radiation. Solving the set of equations, (S6)-(S8), in conjunction with equation (S4), $$R_{ab} = \frac{(\gamma_{ae})^2}{|D_{ab}|^2} \quad (S9)$$

$$D_{ab} = \frac{|\mu|^2 - (v-v_a)(v-v_b) +}{\gamma_a \gamma_{b0} + j[(\gamma_a(v-v_b) + \gamma_{b0}(v-v_a)]} \quad (S10)$$

where $\gamma_a=\gamma_{a0}+\gamma_{ae}$.

When equation (S9) was fit to aqueous solution data to extract the resonator parameters the values for $v_b$ and $\gamma_b$ were held fixed at those representative for the OH bend mode while those characteristic of the plasmonic resonator ($v_a$, $\gamma_{a0}, \gamma_{ae}$) and the coupling rate $\mu$ were allowed to vary.

Constrained Base-Line Correction Based on a Peak Shift

The step-like base-line in the SEIRA data (see FIGS. 5, 6) is a result of the high-frequency, non-resonant component of the protein refractive index (n∞ in equation (4), see also FIG. 8a). Independent of the resonant absorption bands, this will perturb the plasmonic resonance, inducing a peak shift. As illustrated in FIG. 8, this shift results in a step-like feature when the ratio of the two reflectance curves (i.e. referencing to the previous step) is taken to compute the differential absorbance. Rather than use an arbitrary polynomial function to correct this base-line (as is the typical procedure) we leveraged the physical origin of this feature to constrain the functional form of the base-line correction.

Specifically, if we assume a general Lorentzian form for the shape of the nano-antenna reflectance peak, as indicated by equation (S5), $$L_j(v) = A_j \frac{\Gamma_j^2}{(v_j - v)^2 + \Gamma_j^2} + Const. \quad (S11)$$

the form of the base-line is $$b(v)=L_2/L_1+Bv'+G \quad (S12)$$

where, L1 and L2 are given by equation (S11). Equation (S11) differs from (S5) in the presence of the additional constant (Const.) and that the peak amplitude ($A_j$) can be adjusted independently from the line-width. These changes were used to make the fitting procedure based on equations (S11) and (S12) more generally applicable as well as more intuitive.

In equation (S12), the additional terms bv'+G give the equation of a line, with $v'=(v-\mu)/s$ being a centered and scaled frequency. Ideally, in equation (S12) $b(v)=L_2/L_1$ and B=G=0 according to FIG. 8b. The linear correction terms are added to allow for the case of overall slight baseline drifts in between measurements. In general, if used, these terms were very small. In the current implementation of the procedure, the baseline is fit interactively, through a graphical user interface. The results of the fitting procedure, shown in FIGS. 8c,d, show the proposed functional form to fit the slowly-varying step feature well.

Derivation of Equations for Quantification

FTIR absorption spectroscopy measurements typically rely on Beer's law for a first estimation and interpretation of signals, for which, the transmission varies as $T/T_0=e^{-\alpha d}$ where $T_0$ is the transmittance through the windows with the sample absent, d is the physical thickness of the sample and $\alpha$ is the absorption coefficient ($\alpha=4\pi n_{2i}/\lambda$, $n_{2i}$ being the imaginary part of the sample refractive index). In ATR spectroscopy, an effective path length, $d_e$, is defined, such that, in analogy with Beer's law, the reflectance change can be written as, $R/R_0=e^{-\alpha d_e}$.

For weak absorption, $\Delta T \approx -\alpha d$ and $\Delta R \approx -\alpha d_e$, such that $d_e/d \approx \Delta R/\Delta T$. In keeping with this convention, we first sought to quantify our PIR signals similarly, calculating an effective path length from our data. The expected $\Delta T$ can be computed using IRRAS measurements, which controls for the surface selection rule, sample preparation and chemical effects.

To do so, we first note that for a material with a dielectric function described by equation (4), the corresponding refractive index is $n_2=\sqrt{\epsilon_2}=\sqrt{\epsilon_{2r}+j\epsilon_{2i}} \approx n_{2r}+j\epsilon_{2i}/2n_\infty$ if we assume $\epsilon_{2i} \ll \epsilon_{2r}$ and $n_{2r} \approx n_\infty$. The thin film form of the Beer's law transmittance then becomes, $$\Delta T \approx d\left(\frac{2\pi}{\lambda}\right)\left(\frac{\epsilon_{2i}}{n_\infty}\right) \quad (S13)$$

This can then be related to the thin film form of the IRRAS reflection, $$\frac{\Delta R}{R_0} \approx d\left(\frac{8\pi}{\lambda}\right)\left(\frac{\sin^2\theta}{\cos\theta}\right)\text{Im}\left(\frac{-1}{\epsilon_{2i}}\right) \quad (S14)$$

For a protein, $n_\infty \approx 1.45$-$1.5$, so that, $$\text{Im}\left(\frac{-1}{\epsilon_{2i}}\right) \approx \frac{\epsilon_{2i}}{n_\infty^4} \quad (S15)$$

should be used. From equations (S13), (S14) and (S15), we can use, $$\Delta T \approx \frac{n_\infty^3}{4}\frac{\cos\theta}{\sin^2\theta}\Delta R_{(IRRAS)} \quad (S16)$$

Immuno Assay Design

The biochemical properties which determine the differing levels of binding we designed for in FIG. 5 are detailed in the following, beginning with the attachment of the biotin-labeled anti-Rabbit (Goat host), $^{(b)}\alpha R(G)$ (B7389, Sigma) (step 2 in the assay described in FIG. 5).

The $^{(b)}\alpha R(G)$ labeled through its amine groups (reaction with NHS-biotin). When bound to SA, it is expected that it therefore forms a randomly oriented layer. This is significant as IgG is a Y-shaped protein, consisting of a stem (Fc) and two arms (Fab fragments). Roughly speaking, the antigen binding sites are located at the tips of the Fab fragments, therefore only IgGs with these segments sufficiently exposed and oriented outwards will be active for binding a target molecule. Since IgG is roughly 3 times the size of SA (150 vs 50 kDa), steric considerations prevent there from being a one-to-one correspondence between the number of SA and IgG molecules. Therefore, the IgG layer is expected to be much more loosely packed than the SA layer. This is consistent with the observation in FIG. 5f that the $^{(b)}\alpha R(G)$ signal amplitude is very stable from measurement to measurement. The looser packing results additionally in the smaller signal for the IgG molecule, consistent with our SPR measurements (FIG. 12).

The final step in our assay was the binding of one of three target IgG molecules: 1. anti-Goat raised in Mouse, $\alpha G(M)$ purchased from Pierce (31107, Pierce); 2. Rabbit IgG from serum, R(s) (15006, Sigma); and 3. Mouse IgG from serum (15831, Sigma), M(s). These were selected to provide different levels of binding to the $^{(b)}\alpha R(G)$ the basis of their recognition properties in conjunction with the random orientation of the immobilized $^{(b)}\alpha R(G)$. The $\alpha G(M)$ recognizes the surface bound IgG. Since recognition is due to the binding sites of the IgG in solution, the orientation of the surface bound IgG is irrelevant, and one should expect roughly 1 $\alpha G(M)$ per $^{(b)}\alpha R(G)$. Recognition for the R(s) proceeds in the opposite direction, with the antigen binding sites of the surface bound $^{(b)}\alpha R(G)$ recognizing the R(s) in solution. Here the orientational effects mentioned previously are critical. For a randomly oriented layer, $\sim\frac{1}{3}$ of the IgGs might be capable of binding, but efficiencies may be even less than this. Finally, with M(s) there is no recognition in either direction, thus no specific binding. The lack of any signal in this case serves as a negative control and shows that non-specific binding does not result in measurable signals above our current noise level.

In addition to the protein binding assays, FIG. 6 demonstrates the importance of the chemical sensitivity of FTIR in conjunction with the acute sensitivity and versatility of our PIR approach. The selection of latex beads here was motivated by a desire for (1) high frequency refractive index similar to that of proteins (n~1.45); (2) Lack of amide bonds/presence of other vibrational modes near the amide region, within the bandwidth of our plasmonic enhancement; and (3) Comparable surface chemistry/binding protocols such that they could be introduced in our flow device instead of proteins, holding all else constant. These considerations were all ideally satisfied by the biotin-labeled latex beads.

Local Heating Effects

For the measurement of biological samples, thermal damage and denaturing of proteins is an important concern. Although in the visible, spectroscopy can be performed with high-powered and tightly focused lasers, which can appreciably heat samples the low power and large divergence of a Globar source as used in this invention limits the temperature increase, even in the presence of plasmonic resonances. This can be confirmed by considering the heating effects within the uniform temperature approximation (UTA) framework. The approximation is based on the fact that heat flows much faster inside/throughout the nano particle than in the dielectric environment outside it (e.g. water). Therefore, even though the spatial distribution of the absorbed power density is non-uniform, the temperature at the surface of the nano particle is very uniform. This reasonable for e.g. Au particles in water, due to the fact that the thermal conductivity of gold ($\kappa_{Au}$=318 Wm$^{-1}$K$^{-1}$) is significantly larger than that of water ($\kappa_{H2O}$=0.6 Wm$^{-1}$K$^{-1}$).

Within the UTA, the temperature change at the nanoparticle surface is given by $$\Delta T_{NP} = \frac{P_{Abs}}{4\pi R_{eq}\beta\kappa} \quad (S17)$$

where P is the power absorbed (in W), $R_{eq}$ is an equivalent radius corresponding to that of a sphere with the same volume as the nano particle, $\beta$ is a shape function (dimensionless) and $\kappa$ is the thermal conductivity of the ambient. For a Globar source, the power density in a $\Delta\nu$=1 cm$^{-1}$ bandwidth is <1 nW µm$^{-2}$. In particular, approximately 10$^{-9}$ W of power (in a narrow, ~1 cm$^{-1}$ bandwidth) is transmitted through a 10 µm diameter pinhole. This corresponds to an intensity of 1.3×10$^{-11}$ W/µm$^2$ per 1 cm$^{-1}$. Using this as a starting point, we note that the unit cell size for our nano-antenna arrays is 2.5×2.5 µm$^2$. Assuming this is commiserate with the extinction cross section of our nano-antennas, the power delivered per unit bandwidth is P=8×10$^{-11}$ W. Considering the functional form of the plasmonic resonances (i.e. equation (S1)) the absorption from the nano-antenna can be approximated by a Lorentzian, $$A(v) = A_0 \frac{\gamma_A^2}{(v-v_0)^2 + \gamma_A^2} \quad \text{(S18)}$$

$$= (\pi A_0 \gamma_A) \frac{1}{\pi} \frac{\gamma_A}{(v-v_0)^2 + \gamma_A^2}$$

So that $\int_{-\infty}^{\infty} A(v) dv = \pi A_0 \gamma_A$ since $$\int_{-\infty}^{\infty} \frac{1}{\pi} \frac{\gamma_A dv}{(v-v_0)^2 + \gamma_A^2} = 1$$

is the standard normalization. Letting $A_0 \approx 0.3$, $\gamma_A = 200$ cm$^{-1}$ (representative values for our arrays, given the experimental peak reflectance of ~0.7), we find the total absorbed power to be $P_{Abs} = 1.5 \times 10^{-8}$ W.

The parameters Req and β in equation (S17) depend on the particle geometry. We assume that the rod has a cylindrical (instead of rectangular) cross section, with a diameter of d=0.15 μm (this is the average of the width and height for our rectangular particles). The parameter $R_{eq}$ is the radius of a sphere with a volume the same as that of the rod shaped particle. Therefore, $R_{eq} = [(3L-d)d^2/16]^{1/3}$ (L is defined as the total length of the rod, which has hemispherical caps at the end). For L=1.8 μm, $R_{eq}$=0.195 μm. The shape factor β is given for a rod as $\beta = 1 + 0.097 \ln^2(L/d)$. For again L=1.8 μm, d=0.15 μm, β=1.6.

Finally, for water, the thermal conductivity is κ=0.6 W m$^{-1}$ K$^{-1}$=0.6×10$^{-6}$ W μm$^{-1}$ K$^{-1}$. Substituting in all values into eq. (S17), we find $\Delta T_{NP} \approx 6.4 \times 10^{-3}$ K. Thus, we do not expect local heating effects to play a role in affecting e.g. protein conformation during measurements with a Globar source.

REFERENCES

1. Griffiths, P. R. & de Haseth, J. A. Fourier Transform Infrared Spectrometry 2nd edn (John Wiley & Sons, 2007).
2. Ramachandran, N., Larson, D. N., Stark, P. R., Hainsworth, E. & LaBaer, J. Emerging tools for real-time label-free detection of interactions on functional protein microarrays. FEBS J. 272, 5412-5425 (2005).
3. Ozkumur, E. et al. Label-free and dynamic detection of biomolecular interactions for high-throughput microarray applications. Proc. Natl Acad. Sci. USA 105, 7988-7992 (2008).
4. Homola, J. Present and future of surface plasmon resonance biosensors. Anal. Bioanal. Chem. 377, 528-539 (2003).
5. Fernandez, D. C., Bhargava, R., Hewitt, S. M. & Levin, I. W. Infrared spectroscopic imaging for histopathologic recognition. Nat. Biotechnol. 23, 469-474 (2005).
6. Nasse, M. J. et al. High-resolution Fourier-transform infrared chemical imaging with multiple synchrotron beams. Nat. Methods 8, 413-416 (2011).
7. Diem, M., Romeo, M., Boydston-White, S., Miljkovic, M. & Matthaus, C. A decade of vibrational micro-spectroscopy of human cells and tissue (1994-2004). Analyst. (Lond) 129, 880-885 (2004).
8. van den Driesche, S., Witarski, W., Pastorekova, S. & Vellekoop., M. J. A quadruple wavelength IR sensor system for label-free tumour screening. Meas. Sci. Technol. 20, 124015 (2009).
9. Rothschild, K. J. FTIR difference spectroscopy of bacteriorhodopsin: toward a molecular model. J. Bioenerg. Biomembr. 24, 147-167 (1992).
10. Barth, A. Infrared spectroscopy of proteins. Biochim. Biophys. Acta 1767, 1073-1101 2007.
11. Kauffmann, E., Darnton, N. C., Austin, R. H., Batt, C. & Gerwert, K. Lifetimes of intermediates in the b-sheet to a-helix transition of b-lactoglobulin by using a diffusional IR mixer. Proc. Natl Acad. Sci. USA 98, 6646-6649 (2001).
12. Zscherp, C. & Heberle, J. Infrared difference spectra of the intermediates L, M, N, and O of the Bacteriorhodopsin photoreaction obtained by time-resolved attenuated total reflection spectroscopy. J. Phys. Chem. B 101, 10542-10547 (1997).
13. Ataka, K., Kottke, T. & Heberle, J. Thinner, smaller, faster: IR techniques to probe the functionality of biological and biomimetic systems. Angew. Chem. Int. Ed. Engl. 49, 5416-5424 (2010).
14. Kazarian, S. G. & Chan, K. L. Micro- and macro-attenuated total reflection Fourier transform infrared spectroscopic imaging. Appl. Spectrosc. 64, 135-152 (2010).
15. Novotny, L. & van Hulst, N. Antennas for light. Nat. Photonics 5, 83-90 (2011).
16. Osawa, M., Ataka, K., Yoshi, K. & Nishikawa., Y. Surface-enhanced infrared
17. spectroscopy: the origin of the absorption enhancement and band selection rule in the infrared spectra of molecules adsorbed on fine metal particles. Appl. Spectrosc. 47, 1497-1502 (1993).
18. Moscovtis, M. Surface-enhanced spectroscopy. Rev. Mod. Phys. 57, 783-826 (1985).
19. Miyake, H., Ye, S. & Osawa, M. Electroless deposition of gold thin films on silicon for surface-enhanced infrared spectroelectrochemistry. Electrochem. Commun. 4, 973-977 (2002).
20. Ataka, K. & Heberle, J. Electrochemically induced surface-enhanced infrared difference absorption (SEIDA) spectroscopy of a protein monolayer. J. Am. Chem. Soc. 125, 4986-4987 (2003).
21. Badura, A. et al. Light-driven water splitting for (bio-) hydrogen production: photosystem 2 as the central part of a bioelectrochemical device. Photochem. Photobiol. 82, 1385-1390 (2006).
22. Ataka, K. & Heberle, J. Biochemical applications of surface-enhanced infrared absorption spectroscopy. Anal. Bioanal. Chem. 388, 47-54 (2007).
23. Jiang, X. et al. Resolving voltage-dependent structural changes of a membrane photoreceptor by surface-enhanced IR difference spectroscopy. Proc. Natl Acad. Sci. USA 105, 12113-12117 (2008).
24. Enders, D. & Pucci, A. Surface enhanced infrared absorption of octadecanethiol on wet-chemically prepared Au nanoparticle films. Appl. Phys. Lett. 88, 184104 (2006).
25. Enders, D., Nagao, T., Nakayama, T. & Aono, M. In situ surface-enhanced infrared absorption spectroscopy for the analysis of the adsorption and desorption process of Au nanoparticles on the SiO2/Si surface. Langmuir 23, 6119-6125 (2007).
26. Adato, R. et al. Ultra-sensitive vibrational spectroscopy of protein monolayers with plasmonic nanoantenna arrays. Proc. Natl Acad. Sci. USA 106, 19227-19232 (2009).
27. Neubrech, F., Pucci, A., Cornelius, T. W., Karim, S., Garćia-Etxarri, A. & Aizpurua, J. Resonant plasmonic and vibrational coupling in a tailored nanoantenna for infrared detection. Phys. Rev. Lett. 101, 157403 (2008).
28. Cubukcu, E., Zhang, S., Park, Y.-S., Bartal, G. & Zhang., X. Split ring resonator sensors for infrared detection of single molecular monolayers. Appl. Phys. Lett. 95, 43113 (2009).
29. Kundu, J., Le, F., Nordlander, P. & Halas, N. J. Surface enhanced infrared absorption (SEIRA) spectroscopy on nanoshell aggregate substrates. Chem. Phys. Lett. 452, 115-119 (2008).
30. Neubrech, F. & Pucci, A. Plasmonic enhancement of vibrational excitations in the infrared. IEEE J. Selected Topics Quantum Electron. 19, 4600809 (2013).
31. Cataldo, S. et al. Hole-mask colloidal nanolithography for large-area low-cost metamaterials and antenna-assisted surface-enhanced infrared absorption substrates. ACS Nano 6, 979-985 (2012).
32. Novotny, L. Effective wavelength scaling for optical antennas. Phys. Rev. Lett. 98, 266802 (2007).
33. Haus, H. A. Waves and Fields in Optoelectronics (Prentice-Hall, Inc., 1984).
34. Fan, S., Suh, W. & Joannopoulos, J. D. Temporal coupled-mode theory for the Fano resonance in optical resonators. J. Opt. Soc. Am. A Opt. Image Sci. Vis. 20, 569-572 (2003).
35. Verslegers, L., Yu, Z., Catrysse, P. B. & Fan., S. Temporal coupled-mode theory
36. Chen, K., Adato, R. & Altug, H. Dual-band perfect absorber for multispectral plasmon-enhanced infrared spectroscopy. ACS Nano 6, 7998-8006 (2012).
37. Peluso, P. et al. Optimizing antibody immobilization strategies for the construction of protein microarrays. Anal. Biochem. 312, 113-124 (2003).
38. Giacomelli, C. E. in Encyclopedia of Surface and Colloid Science Vol. 5 (ed. Somasundaran, P.) 510-531 (Taylor & Francis, 2006).
39. Schuck, P. J., Fromm, D. P., Sundaramurthy, A., Kino, G. S. & Moerner, W. E. Improving the mismatch between light and nanoscale objects with gold bowtie nanoantennas. Phys. Rev. Lett. 94, 017402 (2005).
40. Liu, N. et al. Plasmonic analogue of electromagnetically induced transparency at the Drude damping limit. Nat. Mater. 8, 758-762 (2009).
41. Liu, N. et al. Planar metamaterial analogue of electromagnetically induced transparency for plasmonic sensing. Nano Lett. 10, 1103-1107 (2010).
42. Luk'yanchuk, B. et al. The Fano resonance in plasmonic nanostructures and metamaterials. Nat. Mater. 9, 707-715 (2010).
43. Artar, A., Yanik, A. A. & Altug, H. Multispectral plasmon induced transparency in coupled meta-atoms. Nano Lett. 11, 1685-1689 (2011).
44. Chen, X. W., Agio, M. & Sandoghdar, V. Metallodielectric hybrid antennas for ultrastrong enhancement of spontaneous emission. Phys. Rev. Lett. 108, 1-5 (2012).
45. Shegai, T. et al. Unidirectional broadband light emission from supported plasmonic nanowires. Nano Lett. 11, 706-711 (2011).
46. Yu, N. et al. Light propagation with phase discontinuities: generalized reflection and refraction. Science 334, 333-337 (2011).
47. Artar, A., Yanik, A. A. & Altug, H. Directional double Fano resonances in plasmonic hetero-oligomers. Nano Lett. 11, 3694-3700 (2011).
48. Dregely, D. et al. 3D optical Yagi-Uda nanoantenna array. Nat. Commun. 2, 267 (2011).
49. Palik, E. D. Handbook of the Optical Constants of Solids Vol. 3 (Academic Press, 1988).
50. Mirabella, F. M. in Handbook of Vibrational Spectroscopy Vol. 2 (eds Chalmers, J. M. & Griffiths, P. R.) 1138 (John Wiley & Sons, 2002).
51. Biacore 3000 Concentration Analysis Handbook. edition 1005-12 AB, GE Healthare http://www.biacore.com/life-sciences/service/downloads/Handbooks/index.html (2001).

SUPPLEMENTARY REFERENCES

52. E A Bayer, E Skutelsky and M Wilchek. The Avidin-biotin complex in affinity cytochemistry. Methods in Enzymology, 39:308-315 (1979).
53. G Baffou, R Quidant and F J Garcia de Abajo. Nanoscale control of optical heating in complex plasmonic systems. ACS Nano, 4:709-716 (2010).
54. M J Weida and B Yee. Quantum cascade laser based replacement for FTIR microscopy. Proceedings of the SPIE, no. 79021C (2011).
55. D L Wetzel and S M LeVine. Biological applications of infrared microspectroscopy. In H U Gremlich and B Yan, editors, Infrared and Raman Spectroscopy of Biological Materials. Marcel Dekker, New York, N.Y. (2001).

The invention claimed is:
1. Infrared absorption spectroscopy apparatus including:
an infrared transparent substrate comprising a first and second surface,
an array of plasmonic nano-antennas arranged on the second surface of the infrared transparent substrate,
a flow cell for holding a liquid to allow spectroscopy measurements in a liquid environment, the array of plasmonic nano-antennas being located inside the flow cell, the second surface of the infrared transparent substrate facing the flow cell,
an optical source providing an infrared incident light probe signal incident on at least a part of the array of plasmonic nano-antennas via the second surface of the infrared transparent substrate, and
an optical element to collect reflected infrared light signal reflected by the part of the array of plasmonic nano-antennas arranged on the second surface of the infrared transparent substrate.
2. Apparatus according to claim 1, wherein the array of plasmonic nanoantennas includes a plurality of molecules.
3. Apparatus according to claim 1, wherein the array of plasmonic nanoantennas includes a layer of molecules.
4. Apparatus according to claim 1, wherein the array of plasmonic nano-antennas includes a monolayer or one sole layer of molecules.
5. Apparatus according to claim 2, wherein the molecule is a biomolecule.
6. Apparatus according to claim 1, wherein the infrared transparent substrate is a $CaF_2$ substrate.
7. Apparatus according to claim 1, wherein the infrared transparent substrate forms part of a wall of the flow cell.
8. Apparatus according to claim 1, wherein the flow cell includes a liquid.
9. Apparatus according to claim 1, wherein the flow cell includes an inlet and an outlet for introducing a liquid into the flow cell and removing the liquid from the flow cell.
10. Apparatus according to claim 1, wherein the optical element includes a microscope objective.

11. Apparatus according to claim 1, further including a spectrometer or mid-infrared detector to analyze the light signal reflected by said part of the array of plasmonic nano-antennas.

12. The apparatus according to claim 1, wherein the reflected light signal includes radiation in a range from 3 μm to 20 μm with signals from infrared molecular absorption of biomolecules in the liquid.

13. The method according to claim 1, wherein the incident light probe signal is reflected from the part of the array of plasmonic nano-antennas back into the infrared transparent substrate.

14. Infrared absorption spectroscopy method comprising the steps of:
  providing an infrared transparent substrate comprising a first and second surface, an array of plasmonic nano-antennas being arranged on the second surface of the infrared transparent substrate, the array of plasmonic nano-antennas includes a plurality of molecules,
  providing a flow cell holding a liquid to allow spectroscopy measurements in a liquid environment, the array of plasmonic nano-antennas being located inside the flow cell and in the liquid, the second surface of the infrared transparent substrate facing the flow cell,
  providing an optical source emitting an infrared incident light probe signal incident on at least a part of the array of plasmonic nano-antennas through the second surface of the infrared transparent substrate, and
  providing an optical element to collect a reflected infrared light signal reflected by the part of the array of plasmonic nano-antennas arranged on the second surface of the infrared transparent substrate.

15. Method according to claim 14, wherein the array of plasmonic nano-antennas includes a layer of molecules.

16. Method according to claim 14, wherein the array of plasmonic nano-antennas includes a monolayer or one sole layer of molecules.

17. Method according to claim 14, wherein the molecule is a biomolecule.

18. Method according to claim 14, further including the step of providing the incident light to the infrared transparent substrate at an incident angle of 0 degrees.

19. Method according to claim 14, wherein the infrared transparent substrate is a $CaF_2$ substrate.

20. Method according to claim 14, wherein the infrared transparent substrate forms part of a wall of the flow cell.

21. Method according to claim 14, wherein the flow cell includes a liquid.

22. Method according to claim 14, wherein the flow cell includes an inlet and an outlet for introducing a liquid into the flow cell and removing the liquid from the flow cell.

23. Method according to claim 14, wherein the optical element includes a microscope objective.

24. Method according to claim 14, further including a spectrometer or mid-infrared detector to analyze the light signal reflected by said part of the array of plasmonic nano-antennas.

25. The method according to claim 14, wherein the reflected light signal includes radiation in a range from 3 μm to 20 μm with signals from infrared molecular absorption of biomolecules in the liquid.

26. The apparatus according to claim 14, wherein the incident light probe signal is reflected from the part of the array of plasmonic nano-antennas back into the infrared transparent substrate.

* * * * *

UNITED STATES PATENT AND TRADEMARK OFFICE
CERTIFICATE OF CORRECTION

PATENT NO. : 9,897,542 B2
APPLICATION NO. : 14/336537
DATED : February 20, 2018
INVENTOR(S) : Ronen Adato and Hatice Altug Page 1 of 1

It is certified that error appears in the above-identified patent and that said Letters Patent is hereby corrected as shown below:

On the Title Page

Item (73), should read:
(73) Assignee: ECOLE POLYTECHNIQUE FEDERALE DE LAUSANNE (EPFL), Lausanne (CH)

Signed and Sealed this
Tenth Day of April, 2018

Andrei Iancu
*Director of the United States Patent and Trademark Office*